US006562542B2

(12) United States Patent
Ohkawa et al.

(10) Patent No.: US 6,562,542 B2
(45) Date of Patent: May 13, 2003

(54) IMAGE-FORMING MATERIAL AND NOVEL SULFONIC ACID ESTER DERIVATIVE

(75) Inventors: Atsuhiro Ohkawa, Kanagawa (JP); Seiya Sakurai, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 78 days.

(21) Appl. No.: 09/818,574

(22) Filed: Mar. 28, 2001

(65) Prior Publication Data

US 2002/0037480 A1 Mar. 28, 2002

(30) Foreign Application Priority Data

Mar. 29, 2000 (JP) ....................................... 2000-091943
Mar. 29, 2000 (JP) ....................................... 2000-091995
Sep. 29, 2000 (JP) ....................................... 2000-299364

(51) Int. Cl.[7] .......................... G03C 1/73; G03C 1/705; C07C 309/63; C08F 20/38; G03F 7/004

(52) U.S. Cl. ............................... 430/270.1; 430/271.1; 430/342; 430/914; 430/919; 430/920; 430/921; 430/925; 430/944; 430/945; 430/281.1; 430/287.1; 558/44; 558/56; 558/57; 558/58; 544/299; 544/304; 544/306; 544/319; 546/294; 548/325.1; 548/325.5; 548/335.1; 548/343.5; 252/587; 526/287; 526/288; 526/259; 526/263; 526/265

(58) Field of Search .............................. 558/44, 56, 57, 558/58; 544/299, 304, 306, 319; 546/294; 548/325.1, 325.5, 335.1, 343.5; 526/259, 263, 265, 287, 288; 430/342, 944, 945, 271.1, 270.1, 914, 921, 925, 919, 920, 281.1, 287.1; 252/587

(56) References Cited

U.S. PATENT DOCUMENTS

| | | | | | |
|---|---|---|---|---|---|
| 3,885,963 | A | * | 5/1975 | Monahan | 430/270.1 |
| 5,344,742 | A | * | 9/1994 | Sinta et al. | 430/270.1 |
| 5,429,906 | A | * | 7/1995 | Bowman et al. | 430/945 |
| 6,143,480 | A | | 11/2000 | Obayashi et al. | 430/332 |

FOREIGN PATENT DOCUMENTS

| | | | |
|---|---|---|---|
| EP | 0 909 656 | 4/1999 | B41M/5/36 |
| JP | 2000-343836 | 12/2000 | B41M/5/30 |
| JP | 2000-343837 | 12/2000 | B41M/5/30 |

* cited by examiner

*Primary Examiner*—Janet Baxter
*Assistant Examiner*—Sin J. Lee
(74) *Attorney, Agent, or Firm*—Sughrue Mion, PLLC

(57) ABSTRACT

An image-forming material is described, comprising on an support an acid-generating agent selected from a sulfonic acid ester of a specific structure generating an acid by the action of heat and the polymer thereof, and a compound causing a light absorption change in the absorption region of from 350 to 700 nm by an intramolecular or intermolecular reaction by the action of an acid. The image-forming material has a high sensitivity and excellent storage stability and gives low haze and good images in the case of performing image formation using a high-output laser light. A sulfonic acid ester derivative represented by the formula, $[R^1SO_3CH(R^2)]R^3$ (wherein $R^1$ represents an alkyl group, an aryl group or a heterocyclic group, $R^2$ and $R^3$ each independently represents an alkyl group or an aryl group, excluding that $R^2$ and $R^3$ are simultaneously aryl groups, $R^2$ and $R^3$ may combine to form a ring, and at least one of $R^2$ and $R^3$ has a polymerizing unsaturated group), and a polymer synthesized by the monomer containing it, are also described.

13 Claims, No Drawings

IMAGE-FORMING MATERIAL AND NOVEL SULFONIC ACID ESTER DERIVATIVE

FIELD OF THE INVENTION

The present invention relates to an image-forming material utilizing the coloring (or decoloring) reaction with an acid.

Also, the invention relates to an image-forming material having a coloring layer containing an acid-generating agent generating an acid by the action of heat and a compound forming a light-absorption change by the reaction with an acid, having a high sensitivity, and having a good shelf life.

Furthermore, the invention relates to a sulfonic acid ester derivative that is decomposed by the action of heat, light, etc., to generate an acid.

Also, the invention relates to a sulfonic acid ester derivative that is excellent in the shelf life and efficiently generates an acid by the action of heat, light, etc.

Still further, the invention relates to a novel sulfonic acid derivative capable of providing an image-forming material excellent in the sensitivity, the image quality, the shelf life, etc., by using together with a compound causing changes in the light-absorption, the hydrophilic or hydrophobic property, etc., by the reaction with an acid.

BACKGROUND OF THE INVENTION

Sulfonic acid esters have been widely used as various reactants, etc., in organic syntheses. Also, by utilizing the property of a sulfonic acid ester that the ester is decomposed to generate sulfonic acid, the sulfonic acid ester is used as an acid-generating agent in the field of image formation.

As the acid-generating agent, compounds each generating an acid by the action of heat, light, etc., are known and properly used according to the purposes used. In these compounds, in regard to an acid-generating agent upon heating generating an acid by the action of heat, it is necessary that the storage stability of being not decomposed by heat during storage with the passage of time is compatible with the activity for the acid-generating reaction by heat, or if it is insufficient, the distinguishing property of the region received heat or light and the region of not received heat or light is lowered. Hitherto, the investigation of improving the compatibility of this kind of shelf life with the reactivity of the acid-generating agent upon heating has been made, and the outline thereof is summarized in "Yuki Zairyo (Organic materials) for imaging" (1997) edited by Organic Electronics Material Kenkyu Kai (Research Society) (published by Bunshin Shuppan K.K.), but the content is yet very insufficient in the above-described point, and further improvements have been desired.

Also, recently, with the progress of high-output lasers, the investigations of image-recording media of heat mode using these lasers have been actively carried out. A method of generating an acid by irradiating a laser using a high-output laser and forming images by the acid and a dye precursor is disclosed in EP-A-0909656, but in the method, because in the case of using a high-output laser, the surface of an image-recording medium is partially thermally broken (so-called abrasion), a haze is increased and background staining, etc., are caused, there is a restriction in the increase of a reaction temperature. As the result thereof, the compatibility of the reactivity with the storage stability, that is, the distinguishability as a recording material is also insufficient in a recording system using a laser light, and the developments of the image-recording method and materials having the compatibility for practical use have yet become a problem in the field of imaging technology.

SUMMARY OF THE INVENTION

A 1st object of the present invention is to provide a novel image-forming material having a high sensitivity and being excellent in the storage stability.

A 2nd object of the invention is to provide an image-forming material giving a low haze and a good surface state even in the case of forming images using a high-output laser.

A 3rd object of the invention is to provide a sulfonic acid ester derivative, which is decomposed by the action of heat, light, etc., to generate an acid.

A 4th object of the invention is to provide a sulfonic acid derivative that is excellent in the shelf life and efficiently generates an acid by the action of heat, light, etc.

A 5th object of the invention is to provide a novel sulfonic acid derivative capable of providing an image-forming material excellent in the sensitivity, the image quality, the shelf life, etc., by using together with a compound which causes changes of the light-absorption, the hydrophilic of hydrophobic property, etc. by the reaction with an acid.

As the result of various investigations for attaining the above-described 1st and 2nd objects, the present inventor has found sulfonic acid group-containing compounds which are stable during the storage and effectively generates an acid by the action of heat and light and also found that by using the compound as an acid-generating agent, the objects can be attained. That is, it has been found that the above-described 1st and 2nd objects have been attained by the 1st to 6th aspects of the invention shown below.

Furthermore, it has also been found that the above-described 3rd, 4th, and 5th objects has been attained by the sulfonic acid ester derivative described in the 7th to 9th aspects of the invention shown below.

That is, the 1st aspect of the invention is an image-forming material comprising on a support the acid-generating agent represented by following formula (I) generating an acid by the action of heat or a polymer obtained by copolymerizing the acid-generating agent and a compound causing a change in the absorption region of from 360 to 700 nm by an intramolecular or intermolecular reaction by the action of an acid, (I)

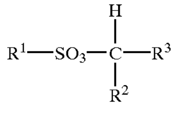

wherein $R^1$ represents an alkyl group, an aryl group, or a heterocyclic group, $R^2$ and $R^3$ each independently represents an alkyl group or an aryl group, excluding that $R^2$ and $R^3$ are simultaneously aryl groups, $R^2$ and $R^3$ may combine to form a ring, and at least one of $R^2$ and $R^3$ has a polymerizing unsaturated group.

The 2nd aspect of the invention is the image-forming material as described in the above-described 1st aspect, wherein the acid-generating agent represented by the above-described formula (I) is represented by following formula (II):

(II)

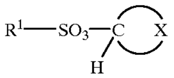

wherein $R^1$ has the same meaning as in the formula (I), X represents an atomic group necessary for forming a ring together with C, and at least one of the atomic group constituting X has a polymerizing unsaturated group.

The 3rd aspect of the invention is the image-forming material as described in the above-described 1st or 2nd aspect, wherein the material comprises a polymer having, as a repeating unit, a partial structure having an acid-generating function obtained by polymerizing the acid-generating agent represented by the formula (I) or (II).

The 4th aspect of the invention is the image-forming material as described in the above-described 3rd aspect, wherein the polymer as described in the 3rd aspect is a polymer represented by following formula (III):

$$-(A)_x-(B)_y-(C)_z- \qquad \text{(III)}$$

wherein A represents a repeating unit obtained by polymerizing the acid-generating agent represented by the formula (I) or (II), B represents a repeating unit obtained by polymerizing at least one kind of a vinyl monomer having a partial structure causing a change in the absorption region of from 360 to 700 nm by the action of an acid, C represents a repeating unit obtained by polymerizing at least one kind of a vinyl monomer polymerizable with A and B, x, y and z represent mol %, each is $1 \leqq x \leqq 100$, $0 \leqq y \leqq 99$, $0 \leqq z \leqq 99$, and $x+y+z=100$.

The 5th aspect of the invention is the image-forming material as described in the above-described 1st to 4th aspects, wherein the image-forming material comprises an infrared absorbing dye and forms images by irradiation of an infrared laser light.

The 6th aspect of the invention is the image-forming material as described in the above-described 1st to 5th aspects, wherein the image-forming layer does not comprise therein a silver compound or the salt thereof.

The 7th aspect of the invention is a sulfonic acid ester derivative represented by following formula (I):

(I)

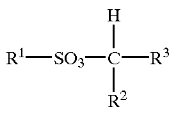

wherein $R^1$ represents an alkyl group, an aryl group, or a heterocyclic group, $R^2$ and $R^3$ each independently represents an alkyl group or an aryl group, excluding that $R^2$ and $R^3$ are simultaneously aryl groups, $R^2$ and $R^3$ may combine to form a ring, and at least one of $R^2$ and $R^3$ has a polymerizing unsaturated group.

The 8th aspect of the invention is the sulfonic acid derivative as described in the above-described 7th aspect, wherein the sulfonic acid ester derivative represented by the above-described formula (I) is represented by following formula (II):

(II)

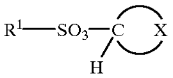

wherein $R^1$ has the same meaning as in the formula (I), X represents an atomic group necessary for forming a ring together with C, and at least one of the atomic group constituting X has a polymerizing unsaturated group.

The 9th aspect of the invention is a polymer obtained by polymerizing the sulfonic acid material represented by the formula (I) of the above-described 7th aspect or the formula (II) of the above-described 8th aspect.

DETAILED DESCRIPTION OF THE INVENTION

Then, the invention is described in detail.

In the formula (I) described above, R represents an alkyl group (methyl, ethyl, n-propyl, isopropyl, t-butyl, n-octyl, dodecyl, cyclopropyl, cyclopentyl, cyclohexyl, [0,1,3] bicyclohexyl, [1,2,2]bicycloheptyl, [1,1,3]bicycloheptyl, etc.), an aryl group (phenyl, naphthyl, etc.), or a heterocyclic group (furyl, thienyl, pyrimidinyl, benzothiazolyl, etc.). In these groups, an alkyl group or an aryl group are preferred and an aryl group is particularly preferred. These groups have from 1 to 18 carbon atoms, and preferably from 1 to 12 carbon atoms excluding a substituent.

Also, these groups each may further have a substituent, as the substituent, any substituent by which a hydrogen can be substituted may be used, and the preferred examples of the substituents include a halogen atom (e.g., fluorine, chlorine, bromine, and iodine), an alkyl group (practically same as described above and further includes a cycloalkyl group and a bicycloalkyl group), an alkenyl group (vinyl, allyl, prenyl, geranyl, oleyl, 2-cyclopenten-1-yl, etc.), an alkinyl group (ethynyl, propargyl, trimethylsilylethynyl, etc.), an aryl group (practical examples are same as described above), a heterocyclic group (practical examples are same as described above), a cyano group, a hydroxyl group, a nitro group, a carboxyl group, an alkoxy group (methoxy, ethoxy, isopropoxy, t-butoxy, n-octyloxy, etc.), an aryloxy group (phenoxy, naphthoxy, etc.), a silyloxy group (trimethylsiyloxy, t-butyldimethylsilyloxy, etc.), a heterocyclic group (pyridyloxy, 2-tetrahydropyranyloxy, etc.), an acyloxy group (formyloxy, acetyloxy, pivaloyloxy, stearoyloxy, benzoyloxy, etc.), a carbamoyloxy group (N,N-dimethylcarbamoyloxy, morpholinocarbonyloxy, N,N-di-n-octylaminocarbonyloxy, N-n-octylcarbamoyloxy, etc.), an alkoxycarbonyloxy group (methoxycarbonyloxy, ethoxycarbonyloxy, t-butoxycarbonyloxy, n-octylcarbonyloxy, etc.), an aryloxycarbonyloxy group (phenoxycarbonyloxy, etc.), furthermore, an amino group (including an anilino group, amino, methylamino, dimethylamino, anilino, N-methylanilino, diphenylamino, etc.), an acylamino group (acetylamino, pivaloylamino, lauroylamino, benzoylamino, 3,4,5-tri-n-octyloxyphenylcarbonylamino, etc.), a carbamoylamino group (carbamoylamino, N,N-dimethylaminocarbonylamino, N,N-diethylcarbonylamino, morpholinocarbonylamino, etc.), an alkoxycarbonylamino group (methoxycarbonylamino, ethoxycarbonylamino, t-butoxycarbonylamino, n-octadecyloxycarbonylamino, N-methylmethoxycarbonylamino, etc.), an aryloxycarbonylamino group (phenoxycarbonylamino, etc.), a sulfamoylamino group (sulfamoylamino, N,N-dimethylaminosulfonylamino, N-n-octylaminosulfonylamino, etc.), an alkyl- and arylsulfonylamino group (methylsulfonylamino, butylsulfonylamino, phenylsulfonylamino, etc.), moreover, a mercapto group, an alkylthio group (methylthio, ethylthio, n-hexadecylthio, etc.), an arylthio group (phenylthio, etc.), a heterocyclic thio group (2-benzothiazolylthio, 1-phenyltetrazol-5-ylthio, etc.), a sulfamoyl group (N-ethylsulfamoyl, N-(3-dodecyloxypropyl)sulfamoyl, N,N-dimethylsulfamoyl, N-acetylsulfamoyl, N-benzoylsulfamoyl, N-(N''-phenylcarbamoyl)sulfamoyl, etc.), a sulfo group, an alkyl- and arylsulfinyl group (methylsulfinyl, ethylsulfinyl, phenylsulfinyl, etc.), an alkyl- and arylsulfonyl group (methylsulfonyl, ethylsulfonyl, phenylsulfonyl, etc.), an acyl group (acetyl, pivaloyl, 2-chloroacetyl, stearoyl, benzoyl, etc.), an aryloxycarbonyl group (phenoxycarbonyl, etc.), an alkoxycarbonyl group (methoxycarbonyl, ethoxycarbonyl, t-butoxycarbonyl, n-octadecyloxycarbonyl, etc.), a carbamoyl group (carbamoyl, N-methylcarbamoyl, N,N-dimethylcarbamoyl, N,N-di-n-octylcarbamoyl, N-(methylsulfonyl)carbamoyl, etc.), an imido group (N-succinimide, N-phthalimide, etc.), a phosphino group (dimethylphosphino, diphenylphosphino, etc.), a phosphinyl group, a phosphinyloxy group, a phosphinylamino group, and a silyl group (trimethylsilyl, t-butyldimethylsilyl, phenyldimethylsilyl, etc.). These substituents may be further substituted by the above-described substituents.

As the substituent of $R^1$, an alkyl group is most preferred.

Practical examples of $R^1$ are shown below, but the invention is not limited to these examples.

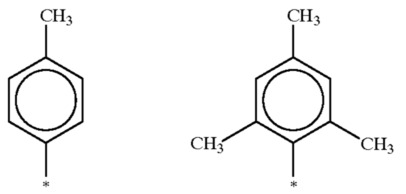

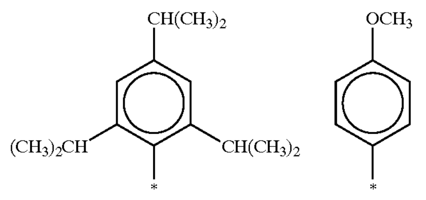

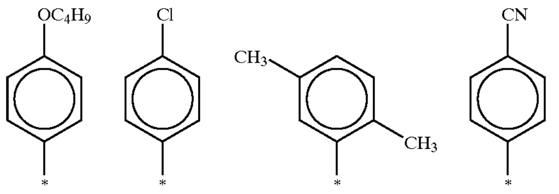

-continued

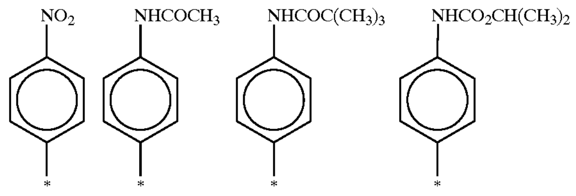

In the above formulae, * shows the position for bonding with —$SO_3$— in the formula (I) or the formula (II), and so forth.

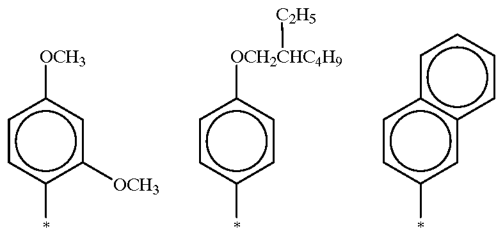

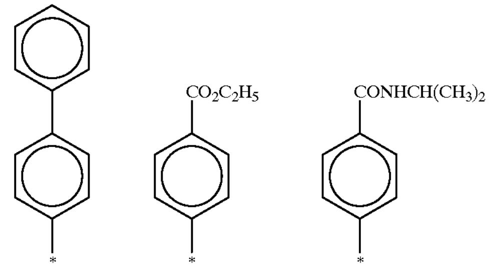

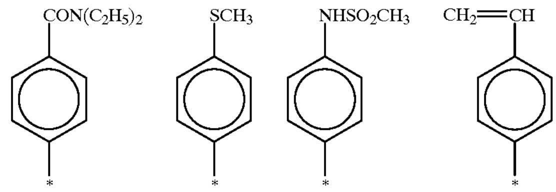

$CH_3$—* $C_8H_{17}$—* $CF_3$—* $(CH_3)_2CH$—* $C_8F_{17}$—*

$C_{12}H_{25}$—*

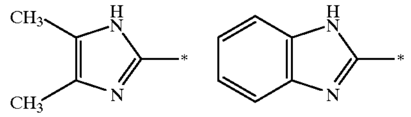

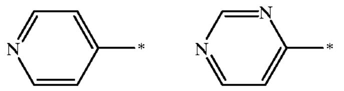

In the formula (I), $R^2$ and $R^3$ each independently represents an alkyl group or an aryl group but it is excluded that $R^2$ and $R^3$ are simultaneously aryl groups. Examples of the alkyl group and the aryl group are same as those described about $R^1$. $R^2$ and $R^3$ each may further have a substituent and the preferred examples of the substituent are those illustrated above as the substituents of $R^1$. Also, at least one of $R^2$ and $R^3$ has a polymerizing unsaturated group. As the polymerizing unsaturated group, a vinyl group is preferred.

Also, $R^2$ and $R^3$ may combine to form a ring. As examples of the sulfonic acid ester of the invention wherein $R^2$ and $R^3$ form a ring, there are various compounds, and the preferred modes thereof are those represented by the formula (II) described above.

In the formula (II), $R^1$ has the same meaning as those in the formula (I). X represents an atomic group necessary for forming a ring together with C and has at least one polymerizing unsaturated group. The polymerizing unsaturated group has the same meaning as those described in the explanation of the formula (I). X forms a ring together with C as described above, as the ring, a 3- to 8-membered rings are preferred, 5- or 6-membered ring is more preferred, and a 6-membered ring is particularly preferred. X is preferably a non-metallic atomic group and more preferably an atomic group formed by linearly bonding plural divalent groups selected from —C($R^4$)($R^5$)—, —C (=Y)—, —N($R^6$)—, —O—, and —S— and these plural divalent groups may be the same or different. The preferred divalent group is —C($R^4$)($R^5$)—. Wherein, $R^4$, $R^5$, and $R^6$ each represents a hydrogen atom or a substituent and preferred examples of the substituent are same as those described above in the explanation of $R^1$. When plural ones of $R^4$, $R^5$, or $R^6$ exist in a molecule, they may be the same or different and also two or more of $R^4$, $R^5$, or $R^6$ may combine to form a ring, Y represents =O, =S, or =N—$R^6$ wherein $R^6$ has the same meaning as those explained above about —N($R^6$)—.

Also, in the compounds represented by the formula (II), more preferred compounds are the compounds represented by following formula (IV).

(IV)

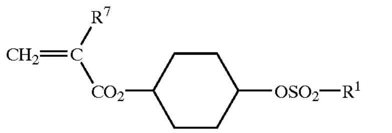

wherein $R^1$ has the same meaning as that in the formula (I), $R^7$ represents a hydrogen atom or an alkyl group, the alkyl group may further have a substituent, and the practical examples of the alkyl group and the substituent are same as those described as the practical examples of $R^1$. $R^7$ is preferably a hydrogen atom or a methyl group.

In the compounds represented by the formulae (I), (II), and (IV), there are compounds wherein isomers such as cis-form isomers, trans-form isomers, etc., exist, and in the invention, they are not specified and also the case of using them as a mixture is included in the invention.

Also, as practically described below in synthesis examples, each of these compounds can be synthesized by the dehydrochlorination of a compound having a hydroxy group and sulfonyl chloride and, in succession, reacting the product and a polymerizing group-containing acyl chloride or after dehydrochlorinating the compound having a hydroxy group and the polymerizing group-containing acyl chloride, by reacting the product and sulfonyl chloride.

Then, polymer compounds induced from the compounds each having a polymerizing group are explained.

When by polymerizing the compounds represented by the formulae (I), (II), and (IV), they show more large ability as functional materials. The molecular weights of the polymers of the invention are preferably in the range of from 1,000 to 1,000,000, and particularly preferably in the range of from 2,000 to 100,000.

The synthesis of the polymer of the invention can be carried out by various polymerization methods such as a solution polymerization, a precipitation polymerization, a suspension polymerization, a bulk polymerization, and an emulsion polymerization. Also, as the initiation method of the polymerization, there are, for example, a method of using a radical initiator and a method of irradiating a light or a radiation. These polymerization methods and the imitation methods of the polymerizations are described, for example, in Teiji Tsuruta, "High Molecule Synthesis Method", revised edition, (published by Nikkan Kogyo Shinbun Sha, 1971) and Takayuki Ootsu and Masaetsu Kinoshita, "Experiment Method of High Molecule Synthesis" published by Kagaku Doojin, 1972, pages 124 to 154.

In the above-described polymerization methods, the solution polymerization method using a radical initiator is particularly preferred. As the solvent used for the solution polymerization, there are, for example, various organic solvents such as ethyl acetate, methanol, ethanol, 1-propanol, 2-propanol, 1-butanol, acetone, dioxane, N,N-dimethylformamide, N,N-dimethylacetamide, benzene, toluene, acetonitrile, methylene chloride, chloroform, and dichloroethane, and these organic solvents may be used singly or as a mixture of two or more kinds thereof, or further may be used as a mixed solvent with water.

It is necessary that the polymerization temperature is established in connection with the molecule weight of the polymer formed, the kind of the initiator, etc., and the polymerization can be carried out at various temperatures but usually the polymerization is carried out at a temperature of from 30 to 100° C. In the invention, it is preferred to carry out the polymerization at a temperature range of from 30 to 90° C.

As the radical initiator used for the polymerization, for example, azo-base initiators such as 2,2'-azobis-isobutyronitrile, 2,2'-azobis(2,4-dimethylvaleronitrile), 2,2'-azobis(2-amidinopropane) dihydrochloride, and 4,4'-azobis (4-cyanopentanoic acid) and peroxide-base initiators such as benzoyl peroxide, t-butyl hydroperoxide, and potassium persulfate (for example, it may be used as a redox initiator by combining with sodium hydrogensulfite) are preferred. In the invention, the initiator wherein the temperature at which the half-life becomes 10 hours is not higher than 70° C. (for example, 2,2'-azobis(2,4-dimethylvaleronitrile), 2,2'-azobis (4-methoxy-2,4-dimethylvaleronitrile), dimethyl-2,2'-azobis(2-methyl propionate), and 2,2'-azobis[2-(3,4,5,6-tetrahydropropane) dihydrochloride] are particularly preferred.

The using amount of the polymerization initiator can be controlled according to the polymerizing property of the monomer used and the molecule weight of the polymer required but is preferably in the range of from 0.01 to 5.0 mol % to the monomer.

Then, practical examples of the compound represented by the formula (I), the formula (II), or the formula (IV) are shown below but the invention is not limited to these compounds. In addition, the number of the homopolymer obtained by polymerizing the monomer shown below is shown by adding P- to the number of the monomer (for sample, the homopolymer of the illustrated compound (1) is shown (P-1). Others are also shown similarly). Also, in some monomers, isomers such as a cis-form isomer, a trans-form isomer, etc., exist, and the cases of polymerizing these mixtures are included in the invention.

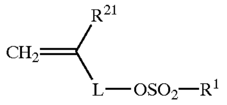
| Compound | $R^{21}$ | L | $R^1$ |
|---|---|---|---|
| 1 | $CH_3$ | 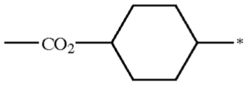 | 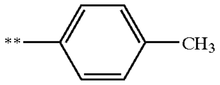 |
| 2 | " | " | 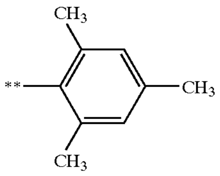 |
| 3 | " | " | 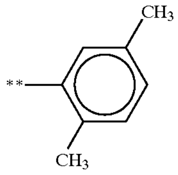 |
| 4 | " | " | 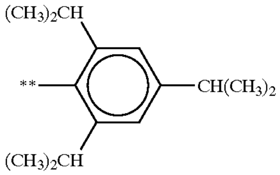 |
| 5 | " | " | 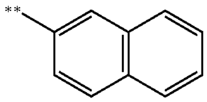 |
| 6 | " | " | 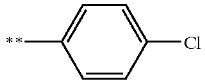 |
| 7 | $CH_3$ | 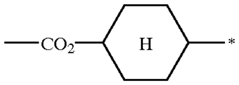 | 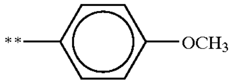 |
| 8 | " | " | 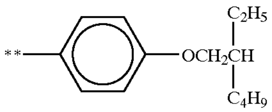 |
| 9 | " | " | 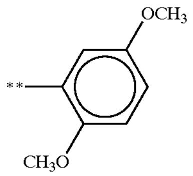 |
| 10 | $CH_3$ | " | $CH_3$ |
| 11 | $CH_3$ | " | $C_8H_{17}$ |

-continued
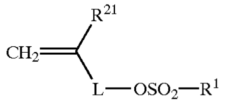
| Compound | $R^{21}$ | L | $R^1$ |
| --- | --- | --- | --- |
| 12 | " | " | 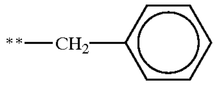 |
| 13 | $CH_3$ | 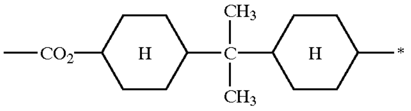 | 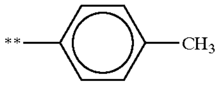 |
| 14 | " | 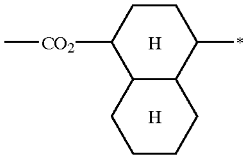 | " |
| 15 | " | 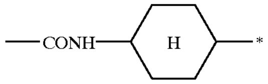 | " |
| 16 | " | 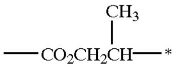 | " |
| 17 | " | 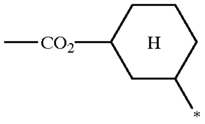 | " |
| 18 | " | 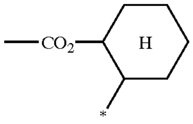 | " |
| 19 | $CH_3$ | 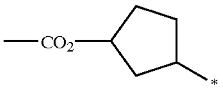 | 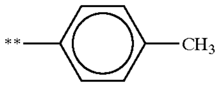 |
| 20 | " | 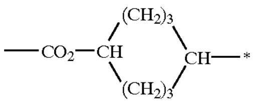 | " |
| 21 | " | 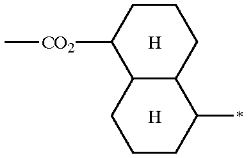 | " |
| 22 | H | 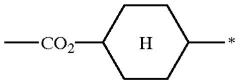 | " |

-continued

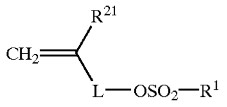

| Compound | $R^{21}$ | L | $R^1$ |
|---|---|---|---|
| 23 | " | 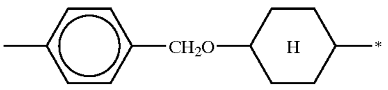 | " |
| 24 | " | 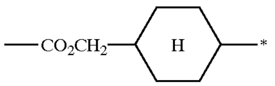 | " |
| 25 | $CH_3$ | 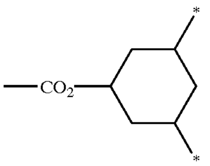 | 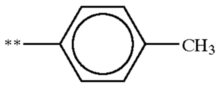 |
| 26 | " | 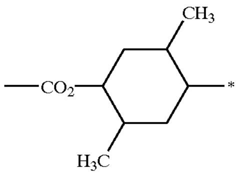 | " |
| 27 | " | 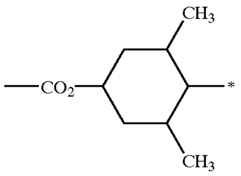 | " |
| 28 | " | 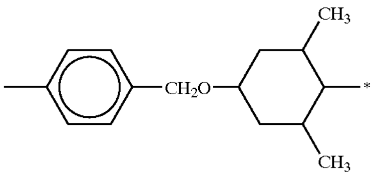 | " |

*shows the bonding position to $—OSO_2—R^1$

**shows the bonding position to $—OSO_2—$ and so forth.

Also, the addition amount of the acid-generating agent differs according to the kind of the compound showing the change of a light absorption used in the invention but, generally speaking, is preferably in the range of from 0.001 to 20 equivalents, and particularly preferably in the range of from 0.01 to 5 equivalents to the compound showing the change of the light absorption region of from 360 to 700 nm by the action of an acid described below.

Then, the compound causing the change of the light absorption of from 360 to 700 nm by causing the intramolecular or intermolecular reaction by the action of an acid is explained.

The compound of accompanying such a light absorption change may be a single compound or may be composed of two or more components. For example, there are (a) a combination of the compounds each forming a fading image in the above-described region by a Diels-Alder reaction (for example, a combination of 9,10-distyrylanthracene and maleic anhydride, a combination of tetraphenylcyclopentadiene and an acrylic acid ester, etc.), (b) a compound forming a color image in the above-described region by a Retrodiels-Alder reaction (for example, an addition product of 9,10-distyrylanthracene and maleic anhydride, an addition product of diphenylisobenzofuran and acrylamide, etc.), (c) a compound forming a color image in the above-described region by spreading of the conjugated system by releasing β-hydrogen (for example, 1-acetoxy-1,2-diarylethane, 1-sulfoxy-1,2-diarylethane, etc.), (d) a combination of an aldehyde forming a color image in the above-described region by a dehydration condensation and an active methylene compound (for example, a combination of a four-equivalent magenta coupler for photography (pyrazolone derivative) and p-methoxycinnamaldehyde) and (e) a compound having an amino group or a hydroxyl group substituted by a substituent the decomposition or releasing of which is accelerated by the action of an acid in the molecule, and changing the light absorption in the above-described absorption region by the decomposition or the release of the above-described substituent.

The substituent of the amino group in the above-described compound of changing the light absorption by decomposing or releasing the substituent of the amino group by the action of an acid includes an alkoxycarbonyl group (e.g., t-butoxycarbonyl, cyclohexyloxycarbonyl, 2-(2-methyl) butoxycarbonyl, 2-(2-phenyl)propyloxycarbonyl, and 2-chloroethoxycarbonyl), an acyl group (e.g., acetyl, benzoyl, 2-nitrobenzoyl, 4-chlorobenzoyl, and 1-naphthyl) and a formyl group, but in the invention, an alkoxycarbonyl group having a hydrogen atom at the β-position is particularly useful in the view points of the storage stability and the heat sensitivity.

Such compounds are described, for example, in U.S. Pat. Nos. 4,602,263 and 4,826,976, and by combining the compound with the acid-generating agent upon heating of the invention and the acid increasing agent, a heat-sensitive image-forming material having a high sensitivity and being excellent in the shelf life can be provided.

The substituent of the hydroxyl group in the compound changing the light-absorption by the decomposition or the release of the substituent of the hydroxyl group by the action of an acid preferably includes a secondary or tertiary alkoxycarbonyl group having a hydrogen atom at the β-position (e.g., t-butoxycarbonyl, isopropyloxycrbomyl, 1-phenylethoxycarbonyl, 1,1-diphenylethoxycarbonyl, and 2-cyclohexeneoxycarbonyl), a silyl group (e.g., trimethylsilyl, triethylsilyl, t-butyldimethylsilyl, t-butyldiphenylsilyl, and phenyldimethylsilyl), an alkoxymethyl group (e.g., methoxymethyl, ethoxymethyl, 1-methoxyethyl, 1-phenoxyethyl, and 2-(2-methoxypropyl)), and a secondary or tertiary alkyl group having a hydrogen atom at the β-position (e.g., tetrahydropyranyl, tetrahydrofuranyl, 4,5-dihydro-2-methylfuran-5-yl, t-butyl, and 2-cyclohexenyl), but in the invention, the secondary or tertiary alkoxycarbonyl group having a hydrogen atom at the β-position is particularly preferred. Examples of the compound changing the light absorption by the decomposition of the substituent of the hydroxyl group are described in U.S. Pat. No. 5,243,052 and JP-A-9-25360 (the term "JP-A" as used herein refers to as an "unexamined published Japanese patent application"), etc.

Also, a basic leuco dye, etc., instantly coloring by the contact with an acid can be used in the image-forming material. As examples of such a compound, there are compounds described in "Imaging Organic Material" edited by Yuki (Organic) Electronics Material Kenkyu Kai, published by Bunshin Shuppan Sha (1997) and compounds described in the cited literatures described therein. Also, the compounds described in Japanese Patent Application Nos. 2000-62402 and 2000-65210 show a high coloring efficiency under the existence of an acid and can be preferably used in the invention.

Then, practical examples of the compound causing the change of the light absorption in the absorption region of from 360 to 700 nm by the action of an acid are shown below, but the invention is not limited to these compounds.

(LD-1)

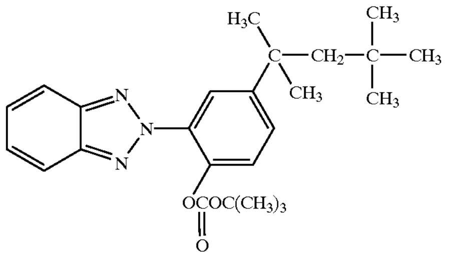

(LD-2)

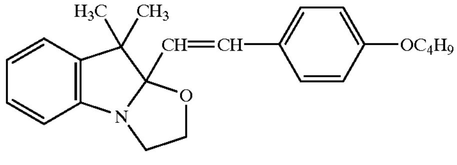

(LD-3)

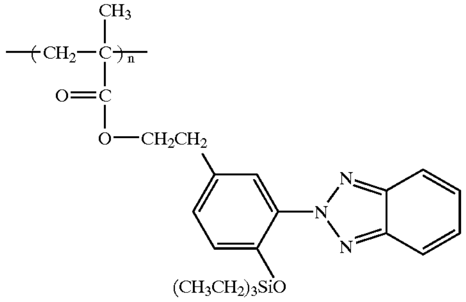

(LD-4)

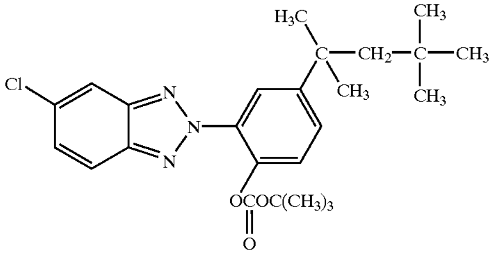

(LD-5)

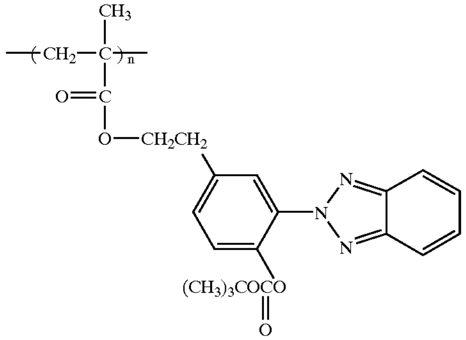

(LD-6)

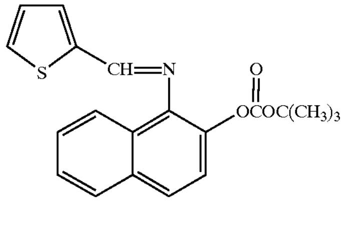

-continued
(LD-7)
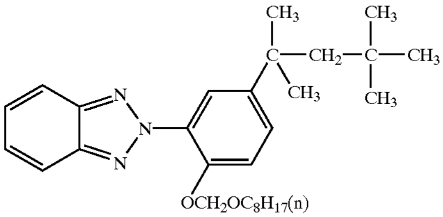
(LD-8)
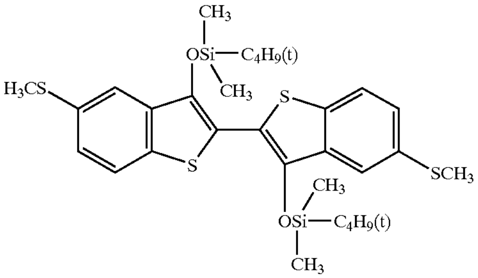
(LD-9)
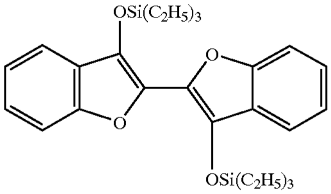
(LD-10)
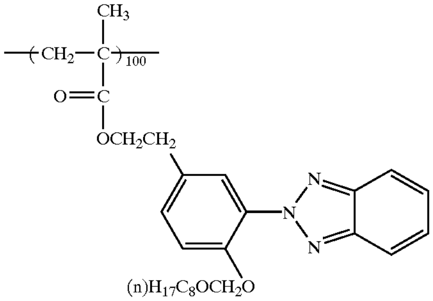
(LD-11)
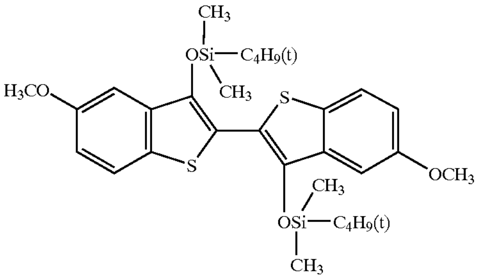
(LD_12)
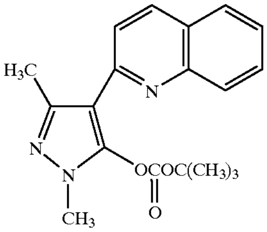
-continued
(LD-13)
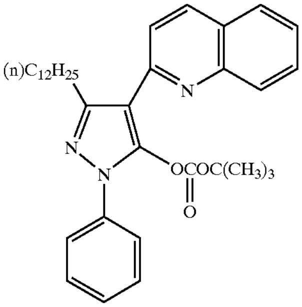
(LD-14)
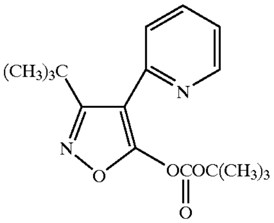
(LD-15)
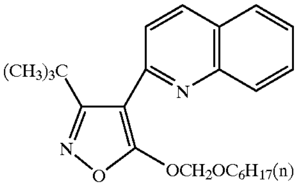
(LD-16)
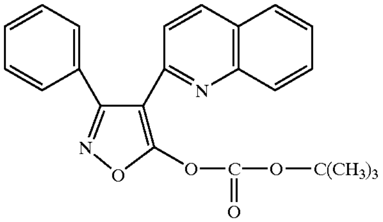
(LD-17)
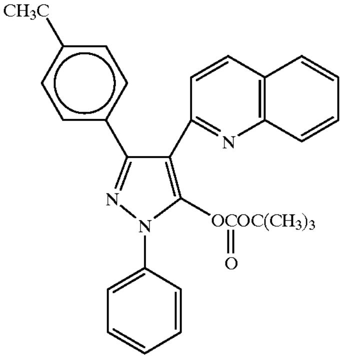
(LD_18)
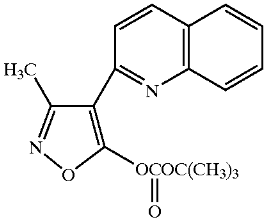

-continued
(LD-19)
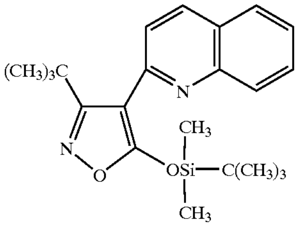
(LD-20)
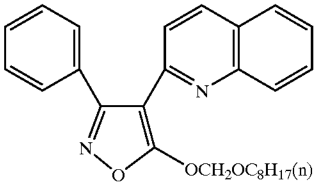
(LD-21)
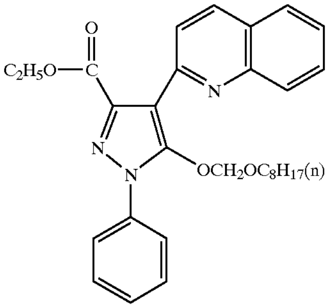
(LD-22)
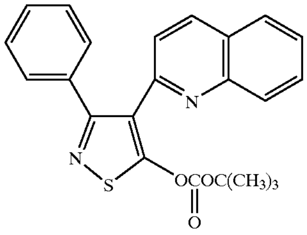
(LD-23)
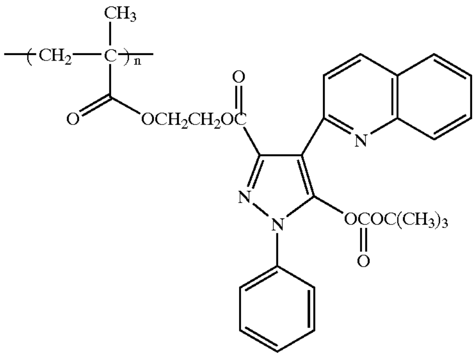
-continued
(LD-24)
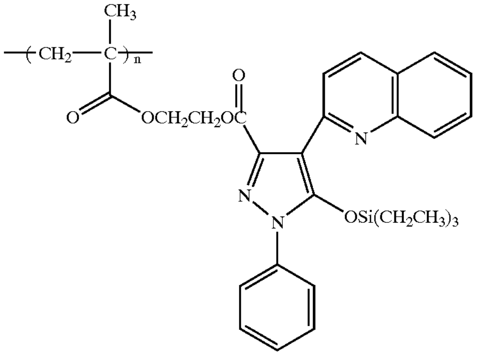
(LD-25)
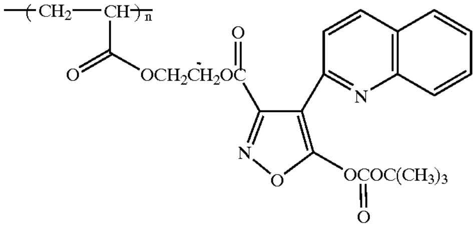
(LD-26)
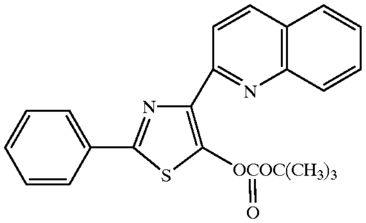
(LD-27)
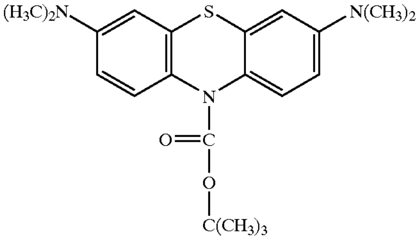
(LD-28)
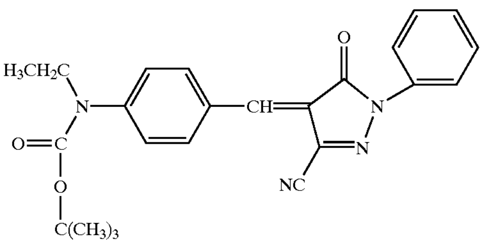

-continued (LD-29)

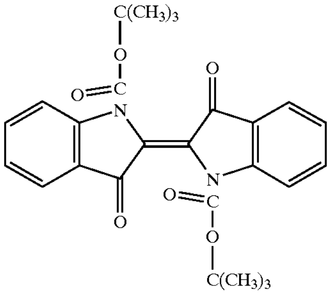

(LD-30)

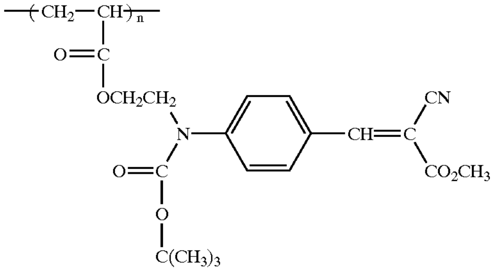

(LD-31)

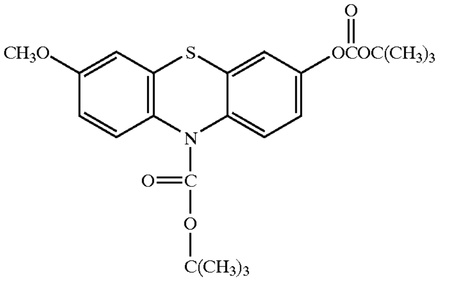

(LD-32)

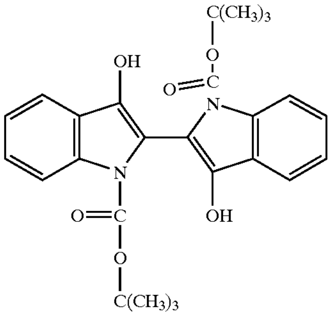

(LD-33)

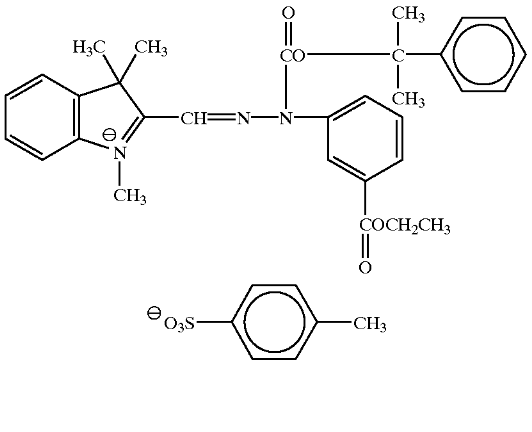

-continued (LD-34)

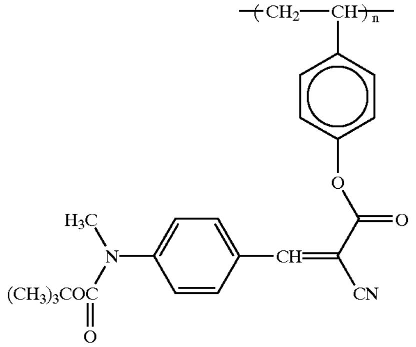

The image-forming material of the invention is generally prepared by coating a solution containing the above-described acid-generating agent and the compound causing the change of the light absorption in the absorption region of from 360 to 700 nm by the action of an acid on a support. In this case, excluding the case that one of them is a polymer or that one of them is an amorphous having a coating property, usually a binder is used together. When the use of a binder is unnecessary, there are merits that the film thickness is liable to be thin and images having good definition are obtained.

Also, when a binder is used, a water-soluble binder such as gelatin, casein, starches, hydroxyethyl cellulose, carboxymethyl cellulose, polyvinyl alcohol, polyacrylamide, an ethylene-maleic anhydride copolymer, etc., or a water-insoluble binder such as polyvinyl butyral, triacetyl cellulose, polystyrene, a methyl acrylate-butadiene copolymer, an acrylonitrile-butadiene copolymer, etc., can be used.

On the other hand, one or both (including copolymer) of the acid-generating agent and the compound causing the change of the light absorption in the absorption region of from 360 to 700 nm by the action of an acid, the addition of a binder is unnecessary. In this case, a high sensitization can be expected in the meaning of generating an acid in the very vicinity of the compound. Also, by controlling the diffusion of the molecule(s) by the polymerization thereof, there is a possibility of improving the resolution and the shelf life of images. These characteristics are particularly preferred for the use of requiring a high image quality such as a graphic art film. A preferred mode of such a compound is represented by the formula (III) described above.

Then, the formula (III) is explained.

In the formula (III), A represents a compound shown by the formula (I), (II), or (IV).

In the formula (III), B represents a repeating unit obtained by the polymerization of at least one kind of a vinyl monomer having the partial structure causing a change of the light absorption in the absorption region of from 360 to 700 by the action of an acid. The compound causing the change of the light absorption by the action of an acid is as described above, and the vinyl monomer relating to B is the compound having introduced a polymerizing group to the position capable of being substituted in the above-described structure. Then, the practical examples thereof are shown below, but the invention is not limited to these compounds.

-continued
(B-1)
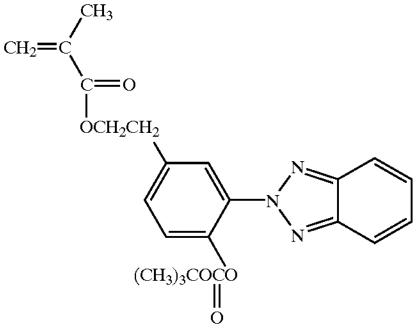
(B-2)
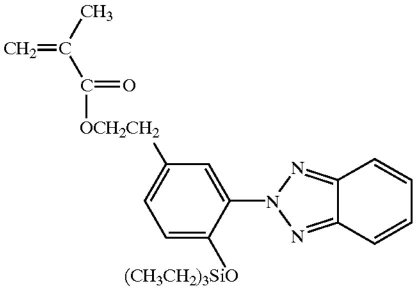
(B-3)
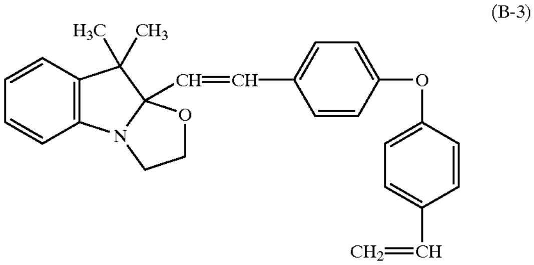
(B-4)
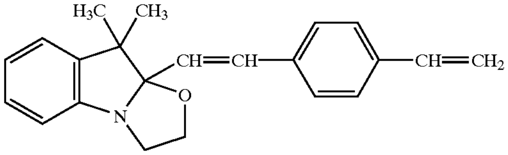
(B-5)
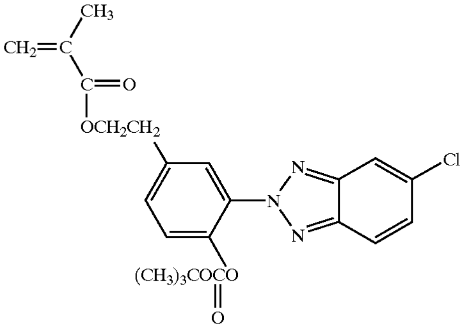
(B-6)
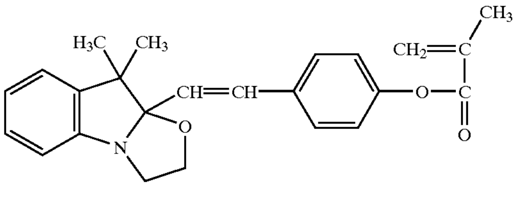
(B-7)
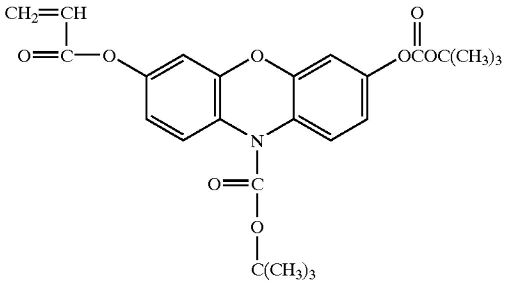
(B-8)
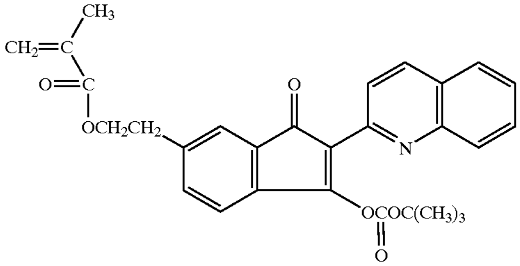
(B-9)
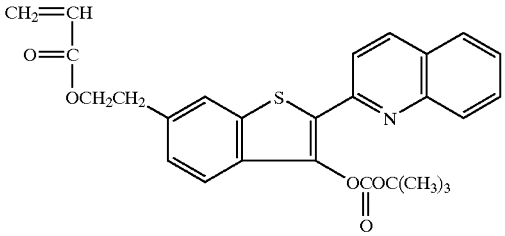
(B-10)
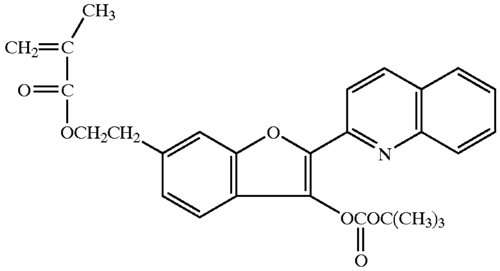
(B-11)
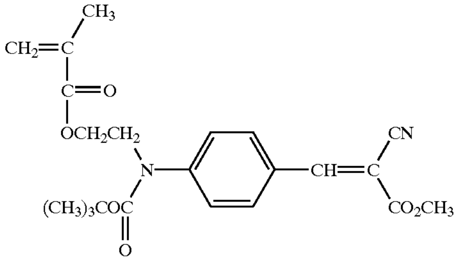

-continued
(B-12)
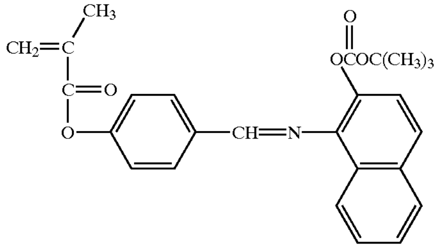
(B-13)
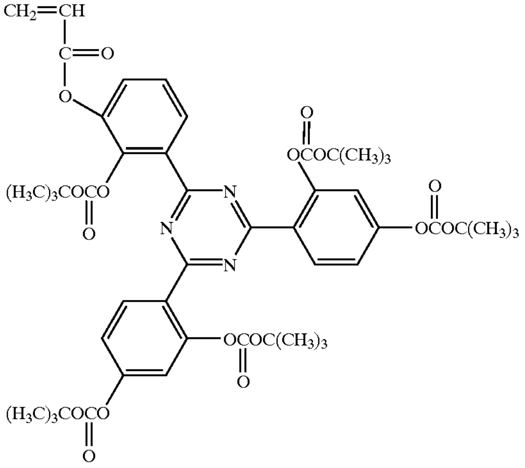
(B-14)
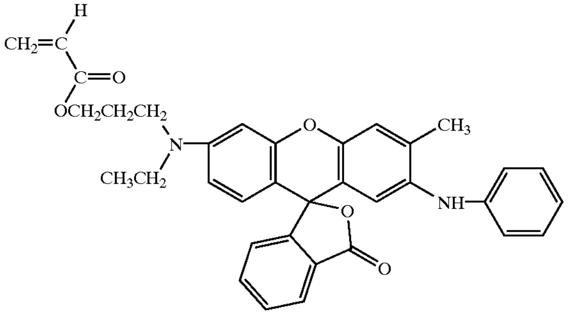
(B-15)
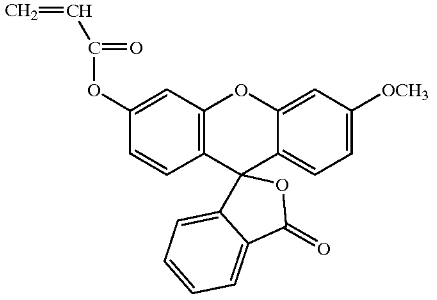
-continued
(B-16)
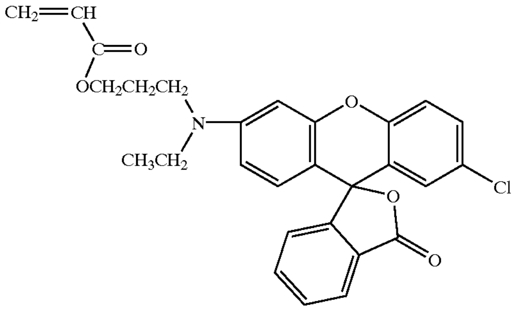
(B-17)
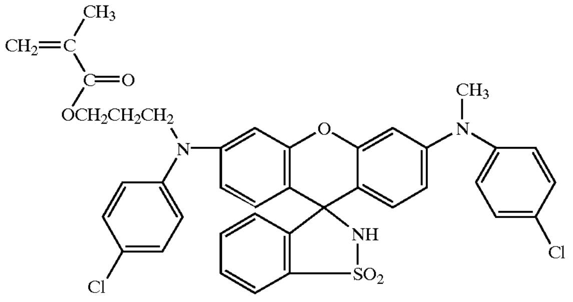
(B-18)
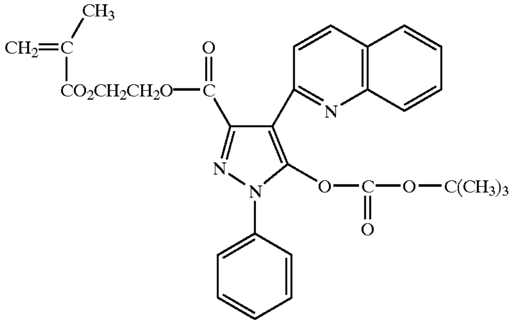
(B-19)
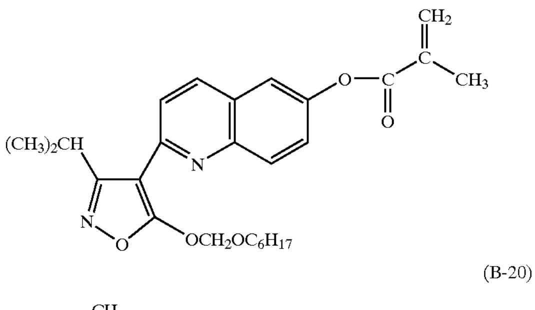
(B-20)
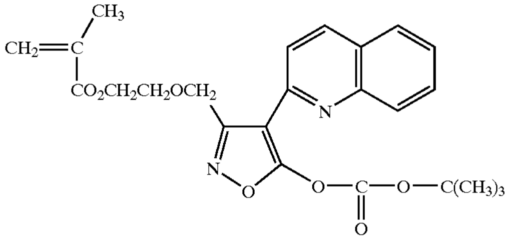

-continued (B-21)

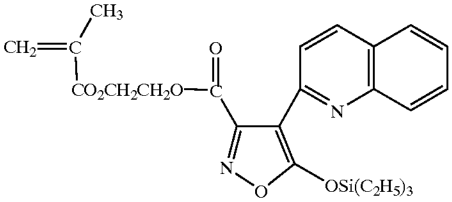

(B-22)

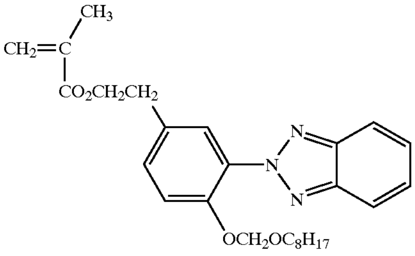

In the formula (III), C represents a repeating unit obtained by the polymerization of at least one kind of a vinyl monomer capable of forming a copolymer with A and B, and by controlling the polarity, the glass transition temperature, etc., thereof, the storage stability, the coloring property, etc., can be controlled. Such vinyl monomers may be used as the combination of two or more kinds of them. As the preferred examples thereof, there are acrylic acid esters, methacrylic acid esters, acrylamide, styrene, and vinyl ethers.

Then, practical examples of the monomer constituting C are shown below but the invention is not limited to them.

(C-1)

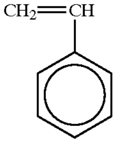

(C-2)

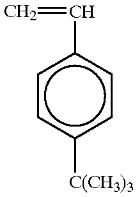

(C-3)

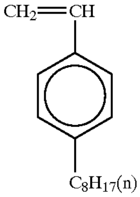

(C-4)

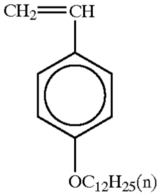

-continued (C-5)

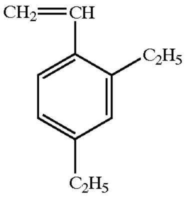

(C-6)

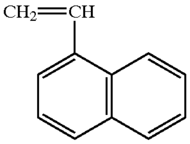

(C-7)

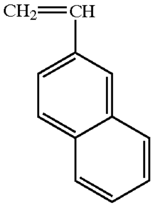

(C-8)

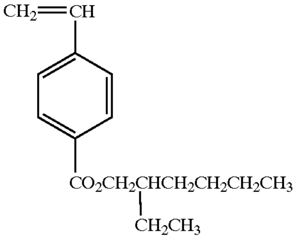

(C-9)

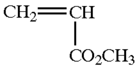

(C-10)

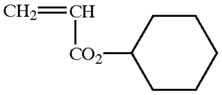

(C-11)

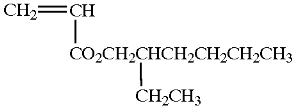

(C-12)

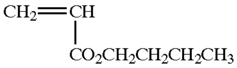

(C-13)

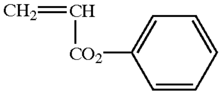

(C-14)

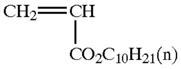

(C-15)

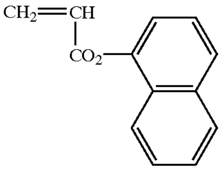

-continued
(C-16)
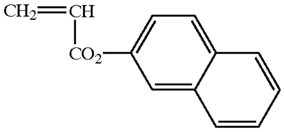
(C-17)
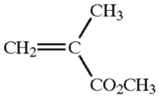
(C-18)
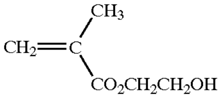
(C-19)
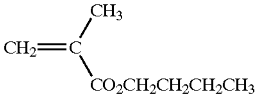
(C-20)
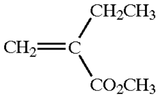
(C-21)
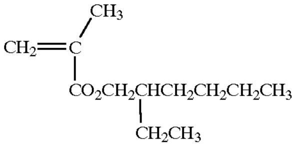
(C-22)
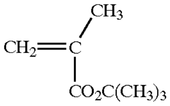
(C-23)
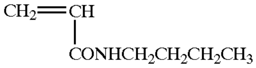
(C-24)
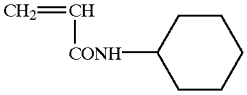
(C-25)
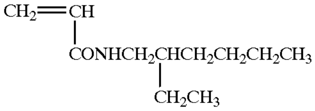
(C-26)
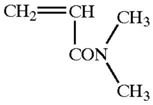
(C-27)
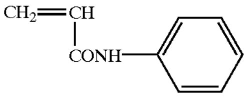
(C-28)
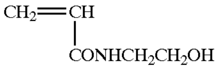
(C-29)
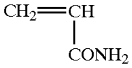
-continued
(C-30)
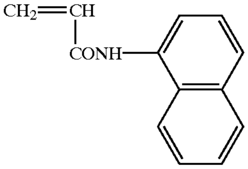
(C-31)
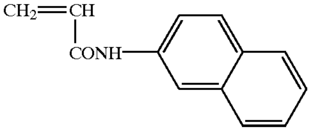
(C-32)
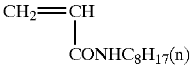
(C-33)
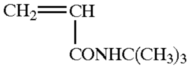
(c-34)
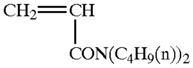
(c-35)
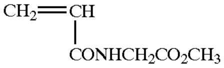
(C-36)
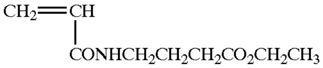
(C-37)
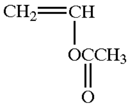
(C-38)
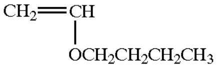
(C-39)
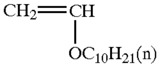
(C-40)
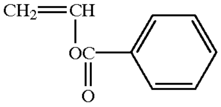
(C-41)
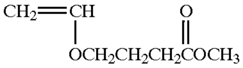
(C-42)
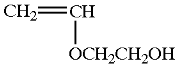
(C-43)
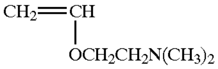
(C-44)
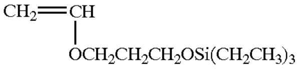
(C-45)
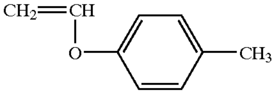

-continued (C-46)

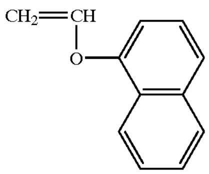

(C-47)

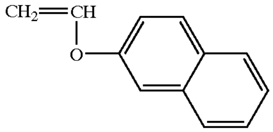

(C-48)

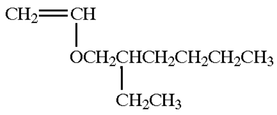

In the formula (III), x, y, and z represent mol % of each composition. Also, x, y, and z each is $1 \leqq x \leqq 100$, $0 \leqq y \leqq 99$, and $0 \leqq z \leqq 99$, and x+y+z=100. Furthermore, z is preferably $0 \leqq z \leqq 90$, and more preferably $0 \leqq z \leqq 50$.

The molecular weight of the polymer represented by the formula (III) is in the range of preferably from 1,000 to 1,000,000, and particularly preferably from 2,000 to 100,000. Also, the polymer may be a homopolymer, a random copolymer, an alternating copolymer, a block copolymer, etc., but a homopolymer and a random copolymer, which can be easily synthesized, are preferred.

Then, preferred combinations of the monomers forming A, B, and C in the polymers represented by the formula (III) and x, y, and z are shown in Table 1 below, but the invention is not limited to these combinations.

TABLE 1

| Sample | A | B | C | x | y | z |
|---|---|---|---|---|---|---|
| CP-(1) | (1) | B-(3) | — | 50 | 50 | |
| CP-(2) | (1) | B-(3) | — | 67 | 33 | |
| CP-(3) | (2) | B-(3) | — | 50 | 50 | |
| CP-(4) | (2) | B-(3) | — | 75 | 25 | |
| CP-(5) | (2) | B-(1) | — | 20 | 80 | |
| CP-(6) | (2) | B-(1) | — | 50 | 50 | |
| CP-(7) | (2) | B-(14) | — | 20 | 80 | |
| CP-(8) | (2) | B-(22) | — | 20 | 80 | |
| CP-(9) | (2) | B-(19) | — | 20 | 80 | |
| CP-(10) | (2) | B-(19) | — | 40 | 60 | |
| CP-(11) | (15) | B-(3) | — | 67 | 33 | |
| CP-(12) | (13) | B-(3) | — | 67 | 33 | |
| CP-(13) | (2) | B-(3) | C-(9) | 60 | 20 | 20 |
| CP-(14) | (2) | B-(3) | C-(17) | 60 | 20 | 20 |
| CP-(15) | (2) | B-(3) | C-(18) | 22.5 | 67.5 | 10 |

The syntheses of these polymers are as described in the explanations of the formulae (I), (II), and (IV).

In the synthesis of the polymer represented by the formula (III) the monomers forming A, B, and C respectively are mixed and first placed in a reaction vessel and an initiator may be added thereto, or the polymerization may be carried out through the course of adding dropwise the monomers to a polymerization solvent.

The polymer represented by the formula (III) in the invention is a polymer having together a partial structure having a function of generating an acid by the action of heat or an acid and a partial structure causing the change of the light absorption in the absorption region of from 350 to 700 nm by the action of acid. As such a polymer, there can exist a polymer of a single monomer having both the functions described above, but from the view point of the synthesis, the polymer represented by the formula (III) is advantageous and the polymer represented by the formula (III) is preferred because the selective range of the monomers to be used is widened.

The image-forming material of the invention is generally prepared by coating polymer represented by the formula (III) on a support. When the polymer of the invention has a function of generating an acid by the action of heat, the change of the light absorption is independently caused in the absorption region by only the action of heat, whereby when the polymer is used for a heat-sensitive image-forming material, the sensitivity and the resolution of the image formed are excellent. Also, because in the image-forming material of the invention, the above-described polymer itself has a function of a binder, the binder as described above may not be used, whereby there are advantages that the film thickness can be thinned, images having a good resolution are obtained, and a thermal breakage, that is, an abrasion is hard to occur. However, in the case of using the polymer represented by the formula (III), if necessary, a binder may be used and as the practical examples of the binder, there are those described above.

In the present invention, for the purpose of increasing the storage stability of the image-forming material, a small amount of a base can be added, for the purpose of increasing the sensitivity, a compound generating an acid by the action of light or heat can be additionally added, and, if necessary, various additives such as a pigment, an antioxidant, a sticking inhibitor, etc., can be added. Also, for protecting the image-forming layer, an overcoat may be formed and a backcoat layer may be formed on the back surface of the support. In addition, various known techniques in heat-sensitive image-forming materials, such as a single layer or plural layers of undercoat layers containing a pigment or made of a resin are formed between the image-forming layer and the support.

In the case of using a protective layer in the invention, there is no particular restriction on a binder used for the protective layer if it is colorless and is a medium forming a transparent or translucent film and examples of the binder include water-soluble binders such as gelatin, casein starches, hydroxyethyl cellulose, carboxymethyl cellulose, polyvinyl alcohol, polyacrylamide, an ethylene-maleic anhydride copolymer, etc., and water-insoluble binders such as polyvinylbutyral, triacetyl cellulose, cellulose acetate butyrate, polyesters, polycarbonates, polyvinylesters (polyvinyl acetate, etc.), polystyrene, polyvinyl chloride, an acrylic acid ester and methacrylic acid ester polymer or copolymer (e.g., a methyl methacrylate-hydroxymethyl methacrylate copolymer, a methyl acrylate-butadiene copolymer, polymethyl methacrylate, poly t-butyl methacrylate, and an acrylonitrile-butadiene copolymer), etc.

In these binders, the water-insoluble binders are preferably used. The water-insoluble binder may form a film from a solution in an organic solvent or may form a film in the form of an aqueous dispersion. In this case, the aqueous dispersion is a dispersion formed by dispersing the water-insoluble hydrophobic polymer in a water-soluble dispersion medium as fine particles. As the dispersed state, there are states that the polymer is emulsified in the dispersion medium, the polymer is emulsion polymerized, the polymer is micelle-dispersed in the dispersion medium, the polymer partially has a hydrophilic structure in the molecule, and the molecule chain itself is dispersed in a molecular form, etc.

These examples are described in "Synthetic Resin Emulsion" edited by Taira Okuda and Hiroshi Inagaki, published by Kobunshi Kanko Kai (1978), "Application of Synthetic Latex", edited by Takaaki Sugimura, Yasuo Kataoka, Soichi Suzuki, and Keiji Kasahara, published by Kobunshi Kanko Kai (1993), Soichi Muroi, "Chemistry of High-Molecular Latex", published by Kobunshi Kanko Kai (1970), etc. The mean particle size of the dispersed particles is in the range of preferably from 1 to 50,000 nm, and more preferably from about 5 to 1,000 nm. There is no particular restriction on the particle size distribution of the dispersed particles, and the dispersed particles may have a wide particle size distribution or a monodispersed particle size distribution.

The molecular weight of the polymer for the image-forming material and the protective layer is from 1,000 to 1,000,000, and preferably from about 20,000 to 500,000 as a weight average molecular weight. Also, the polymers may be used singly or, if necessary, as a blend of two or more kinds thereof.

Also, by controlling the Tg of the polymer used for the image-forming material and the protective layer, the occurrence of cracks of the image-forming material under a low humidity can be sometimes improved. That is, by lowering the Tg of the polymer, the occurrence of cracks of the image-forming material under a low humidity can be prevented, but because the Tg is too lowered, the adhesive property of the image-forming material sometimes causes a problem, there is the optimum value in the Tg of the polymer. The preferred Tg of the polymer depends upon the kind of a low-molecular compound used together, but is generally from 15° C. to 120° C., and preferably from 20° C. to 80° C.

Also, the occurrence of cracks is remarkable under a low humidity, and in general cracking is frequently evaluated by the radius of rounding the image-forming material in a pipe form at a temperature of 25° C. and a relative humidity of 10% RH at which a crack begins to occur, and the preferred value is not larger than 50 mm.

Furthermore, for the purpose of preventing the occurrence of cracking, a plasticizer can be used. Practically, the plasticizers described in Japanese Patent Application No. 2000-65238 can be preferably used.

Also, a matting agent, a lubricant, etc., cam be used and practically, the compounds described in Japanese Patent Application No. 2000-65238 can be preferably used.

When a base is added to the image-forming layer or the protective layer, an organic base is preferred and preferred examples of the organic base include guanidine derivatives (e.g., 1,3-diphenylguanidine, 1,3-dimethylguanidine, 1,3-dibutylguanidine, 1-benzylguanidine, and 1,1,3,3-tetramethylguanidine), aniline derivatives (e.g., aniline, p-t-butylaniline, N,N-dimethylaniline, N,N-dibutylaniline, and triphenylamine), alkylamine derivatives (e.g., tributylamine, octylamine, laurylamine, benzylamine, and dibenzylamine), and heterocyclic compounds (e.g., N,N'-dimethylaminopyridine, 1,8-diazabicyclo[5,4,0]-7-undecene, triphenylimidazole, lutidine, and 2-picoline). The organic base is added in an amount of preferably from 1 to 50 mol %, and particularly preferably from 5 to 20 mol % to the composition represented by A of the formula (I).

When the image-forming material of the invention is utilized as an image-forming material of a photon mode system, the addition of a compound generating an acid by the action of a light becomes inevitable.

On the other hand, when the image-forming material of the invention is utilized for the image-forming material of a heat mode system, for aiming at obtaining a higher sensitivity, an acid-generating agent may be additionally added. As known acid-generating agents, there are the compounds described in "Imaging Organic Material" edited by Yuki (Organic) Electronics Material Kenkyu Kai, published by Bunshin Shuppan Sha (1997), pages 37 to 91, and the compounds described in the cited literatures described therein. Also, many of the photo-acid-generating agents described therein function as acid-generating agents upon heating.

In the case of adding a pigment, preferred examples of the pigment used in the invention include diatomaceous earth, talc, kaolin, burned kaolin, titanium oxide, silicon oxide, magnesium carbonate, calcium carbonate, aluminum hydroxide, and a urea-formalin resin.

As other additives, there are ultraviolet absorbents of benzophenone-base, benzotriazole-base, etc.; head abrasion and sticking inhibitors made of higher fatty acid metal salts such as zinc stearate, calcium stearate, etc.; waxes such as paraffin, oxidized paraffin, polyethylene, oxidized polyethylene, caster wax, etc., and they can be, if necessary, added to the image-forming material.

The support used for the image-forming material of the invention includes papers such as wood-free papers, baryta papers, coated papers, cast-coated papers, synthetic papers, etc.; polymer films such as the films of polyethylene, polypropylene, polyethylene terephthalate, polyethylene-2,6-naphthylene dicarboxylate, polyarylene, polyimide, polycarbonate, triacetyl cellulose, etc.; glasses, metal foils, nonwoven fabrics, etc.

When the image-forming material of the invention is used for the uses for forming transmission type images such as an OHP film, a plate-making film, etc., a transparent support is used, Also, for the plate-making film, a support having a small thermal expansion coefficient, having a good dimensional stability, and having no absorption in the photosensitive region of a PS plate is selected.

In the image-forming material of the invention, a means for forming images is carried out by heating or a light irradiation of a light to heat energy transforming property, that is, of a so-called heat mode. When the image formation is carried out by heating, as the heating method, a method of contacting with a heated block or plate, a method contacting with a heat roller or a heat drum, or a method of image-wise heating by a thermal head of a heat-sensitive printer is used, and when the image formation is carried out by a light irradiation, in addition to a method of irradiating by a halogen lamp or an infrared or far-infrared lamp heater, there are a method of irradiating a laser light, etc. When the image-forming material of the invention is used for a use of requiring a high resolution such as the use of a plate-making material, etc., a system of scanning exposing by a laser light is preferred. For forming images by a smaller thermal energy, the thermal image-forming material of the invention can be previously heated to a proper temperature. In the present invention, after carrying out image-wise heating by the above-described method, the image can be amplified by heating the whole surface of the image-forming material to a temperature of from 60 to 150° C. (preferably, from 60 to 120° C.).

In the case of forming images by a laser light irradiation, to transform the laser light to a thermal energy, it is necessary to incorporate a dye absorbing the light of the wavelength of the laser light into an image-forming material. As a laser light source, there are an excimer laser, an argon laser, a helium neon laser, a semiconductor laser, a glass (YAG) laser, a carbonic acid laser, a dye laser, etc., and in these lasers, a helium neon laser, a semiconductor laser, and a glass laser is useful laser light sources in the invention. In these lasers, a semiconductor laser is particularly useful because the device is small and inexpensive. The oscillation wavelengths of semiconductor lasers are usually from 670 to 830 nm. Accordingly, for the image-forming material of the invention of carrying out recording by these laser lights, dyes having the light absorption in the near-infrared spectral region are used. As the near-infrared dyes used in the invention include cyanine dyes, squliarium dyes, merocyanine dyes, oxonole dyes, phthalocyanine dyes, etc. Practical examples thereof are described, for example, in U.S. Pat. Nos. 4,973,572, 4,948,777, 4,950,640, 4,950,639, 4,948,776, 4,948,778, 4,942,141, 4,952,552, 5,036,040, and 4,912,083.

Then, synthesis examples of the compounds of the invention are shown below but the invention is not limited to them.

SYNTHESIS EXAMPLE 1

Synthesis of Compound (1)

(100 ml) of 1 mol/liter of hydrochloric acid, dried over magnesium sulfate, and then concentrated. The oily product obtained was purified by a silica gel column chromatography (eluent: ethyl acetate/hexane=1/4→1/1) to obtain a reaction product 1c at the yield of 61%.

Then, the raw material compound 1d (50 mmol) was dissolved in pyridine (30 ml) and the solution was cooled to 7° C. To the solution was added the reaction product 1c (50 mmol) and the mixture was stirred for 8 hours. Thereafter, water (3 ml) was added thereto followed by stirring for 30 minutes, ethyl acetate (100 ml) and water (200 ml) were added thereto followed by stirring, and aqueous layer formed was removed. Furthermore, the organic layer formed was washed three times with an aqueous solution (100 ml) of 1 mol/liter of hydrochloric acid, dried over magnesium sulfate, and concentrated. The oily product obtained was purified by a silica gel column chromatography (eluent: ethyl acetate/hexane=1/4→1/1) to obtain the compound (1) as a mixture of the cis- and trans-isomers at the yield of 72%. Also, the cis-isomer and the trans-isomer can be separated each other by a silica gel column chromatography (eluent:

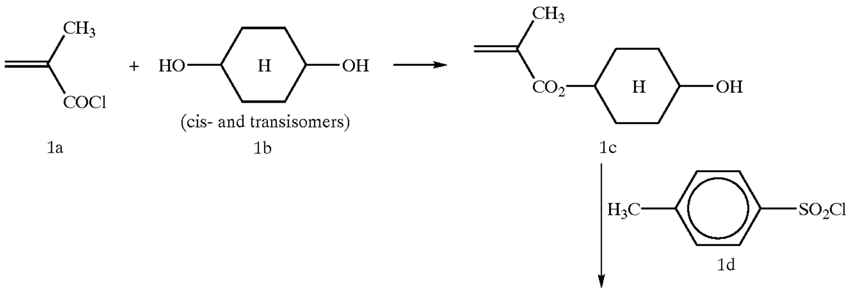

1a 1b (cis- and transisomers) 1c 1d

Compound (1)

The raw material compound 1b (a mixture of cis- and trans-isomers, 100 mmol) was dissolved in N,N-dimethylacetamide (50 ml) in a reaction vessel and the reaction vessel was cooled to 7° C. Then, the raw material la (100 mmol) was added dropwise to the solution over a period of 10 minutes, and thereafter, the reaction mixture was maintained at the temperature for 6 hours to carry out the reaction. Thereafter, ethyl acetate (200 ml) and water (200 ml) were added thereto followed by stirring, and the aqueous layer formed was removed. Furthermore, the organic layer was washed three times with aqueous solution ethyl acetate/hexane=1/4→1/1), and they were separated, and when the decomposition temperature of each isomer was determined, the decomposition temperature of the cis-isomer was 192° C. and that of the trans-isomer was 184° C.

SYNTHETIC EXAMPLE 2

Synthesis of Compound (2)

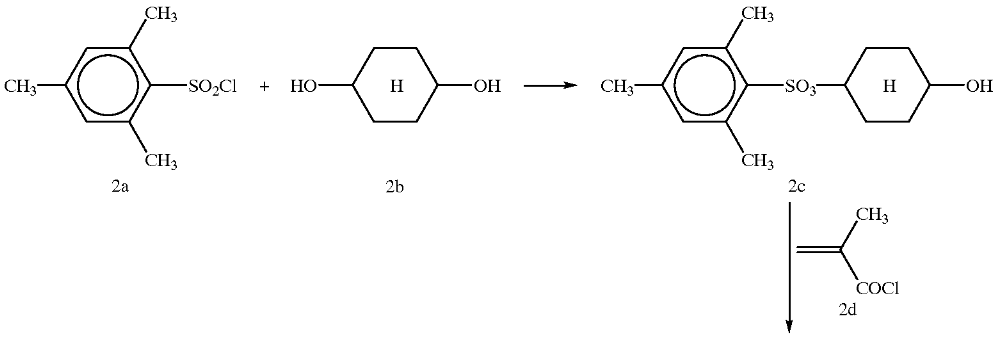

2a 2b 2c 2d

Compound (2)

The raw material compound 2a (100 mmol) was dissolved in pyridine (40 ml) in a reaction vessel, and the reaction vessel was cooled to 7° C. The raw material compound 2b (100 mmol) was added dropwise thereto over a period of 10 minutes, thereafter, the reaction was carried out for 2 hours, and thereafter, the reaction was further carried out for 5 hours at room temperature. Thereafter, after adding water (4 ml) thereto and stirring for 30 minuets, ethyl acetate (150 ml) and water (200 ml) were added followed by stirring, and an aqueous layer was removed. Furthermore, an organic layer formed was washed three times with an aqueous solution (100 ml) of 1 mol/liter of hydrochloride acid, dried over magnesium sulfate, and concentrated. An oily product obtained was purified by a silica gel column chromatography (eluent: ethyl acetate/chloroform=1/8→1/1) to obtain the reaction product 2c at the yield of 76%.

Then, the reaction product 2c (50 mmol) was dissolved in N,N-dimethylacetamide (60 ml) in a reaction vessel and the reaction vessel was cooled to 7° C. The raw material compound 2d (50 mmol) was added dropwise thereto over a period of time of 10 minutes, and thereafter, the reaction was carried out for 8 hours at room temperature. Then, after adding thereto ethyl acetate (200 ml) and water (200 ml) and stirring them, an aqueous layer was removed. Furthermore, an organic layer formed was washed three times with an aqueous solution (100 ml) of 1 mol/liter of hydrochloric acid, dried over magnesium sulfate, and concentrated. An oily product obtained was purified by a silica gel column chromatography (eluent: ethyl acetate/chloroform=1/4→1/1) to obtain the compound (2) as a mixture of the cis-isomer and the trans-isomer at the yield of 78%. The decomposition temperature of the trans-isomer of the compound was 189° C.

SYNTHESIS EXAMPLE 3

Synthesis of Compound (3)

By following the same procedure as the synthesis of the compound (2) in Synthesis Example 2 except that the compound 2a as the starting raw material was changed to 2,5-xylyl-1-sulfonyl chloride, the compound (3) was synthesized as a mixture of the cis-isomer and the trans-isomer. The decomposition temperature of the mixture was 188° C.

SYNTHESIS EXAMPLE 4

Synthesis of Compound (22)

By following the same procedure as the synthesis of Compound (2) in Synthesis Example 2 except that the starting raw material 2a was changed to p-tolylsulfonyl chloride and the raw material 2d was changed to acryl chloride, the synthesis was carried out to obtain a mixture of the cis-isomer and the trans-isomer. The decomposition temperature of the cis-isomer was 182° C. and that of the trans-isomer was 173° C.

SYNTHESIS EXAMPLE 5

Synthesis of Compound (13)

By following the same procedure as the synthesis of the compound (2) in Synthesis Example 2 except that the starting raw material 2a was changed to p-tolylsulfonyl chloride and the raw material 2d was changed to 4-[2-(4-hydroxybutyl-cyclohexyl)propyl]cyclohexanol, the compound (13) was obtained as a mixture of the cis-isomer and the trans-isomer. The clear peak of the decomposition temperature of the mixture was not obtained.

SYNTHESIS EXAMPLE 6

Synthesis of Polymer (P-1)

Polymer (1) (50 mmol) was dissolved in toluene (22 ml) and the solution was heated to 40° C. under a nitrogen atmosphere. After adding thereto a methyl ethyl ketone (3 ml) solution of 2,2'-azobis(4-methoxy-2,4-dimethylvaleronitrile) (0.125 g) and carrying out the reaction for 2 hours, a methyl ethyl ketone (3 ml) solution of 2,2'-azobis(4-methoxy-2,4-dimethylvaleronitrile) (0.125 g) was further added thereto. After carrying out the reaction for 2 hours, the reaction liquid was poured to hexane (1200 ml), precipitates formed were collected by filtration and dried to obtain the polymer (P-1) at the yield of 89%. The weight average molecular weight was 85,000 and the decomposition temperature was 172° C.

SYNTHESIS EXAMPLE 7

Synthesis of Polymer (P-2)

By following the same procedure as the synthesis of the polymer (P-1) using the compound (2), the polymer (P-2) was synthesized. The weight average molecular weight was 120,000 and the decomposition temperature was 187° C.

SYNTHESIS EXAMPLE 8

Synthesis of Polymer (P-3)

By following the same procedure as the synthesis of the polymer (P-1) using the compound (3), the polymer (P-3) was synthesized. The weight average molecular weight was 100,000 and the decomposition temperature was 174° C.

SYNTHESIS EXAMPLE 9

Synthesis of Polymer (P-22)

By following the same procedure as the synthesis of the polymer (P-1) using the compound (22), the polymer (P-22) was synthesized. The weight average molecular weight was 175,000 and the decomposition temperature was 165° C.

SYNTHESIS EXAMPLE 10

Synthesis of Compound (CP-4)

The compound 2 (7.5 mmol) constituting the partial structure A in the formula (III) and the compound B-3 (2.5 mmol) constituting the partial structure B were dissolved in toluene (4.4 ml) methylene chloride (2 ml) and methylene chloride (4 ml), and the solution was heated to 40° C. in a nitrogen atmosphere. To the solution was added a methyl ethyl ketone (0.6 ml) solution of 2,2'-azobis(4-methoxy-2, 4-dimethylvaleronirile) (0.025 g), and after carrying out the reaction for 2 hours, a methyl ethyl ketone (0.6 ml) solution of 2,2'-azobis (4-methoxy-2, 4-dimethylvaleronirile) (0.025 g) and methylene chloride (2 ml) were further added hereto. After carrying out the reaction for 2 hours, the reaction liquid was poured to hexane (400 ml), precipitates deposited were collected by filtration and dried to obtain the compound (CP-4) at the yield of 53%. The weight average molecular weight was 45,000.

Then, the usefulness of the compounds of the invention are explained in detail by the following examples but the invention is not limited to these examples.

Example 1

<Preparation of Image-Recording Film>

The compounds (the coated amounts are shown in Table 2) shown in Table 2 were dissolved in chloroform and the solution was coated on a polyethylene terephthalate film of 175 μm thick. The film was coated with each of the coating liquids 1 to 3 for protective layer shown below by the combination shown in Table 2 below to prepare image-forming materials 1 to 6. For the polystyrene, polystyrene beads (diameter: about 3.2 mm) manufactured by Wako Pure Chemical Industries, Ltd. were used.

<Preparation of Protective Layer Coating Liquids 1 to 3>

The protective layer coating liquids 1 to 3 shown below were prepared and each coating liquid was coated on each image-forming material by the combination described in Table 2. In addition, the protective layer coating liquids 2 and 3 were the protective layer coating liquids PC-5 and PC-6 described in the examples of Japanese Patent Application No. 2000-65238 prepared by the methods described therein.

(Protective Layer Coating Liquid 1)

An aqueous solution containing 4% by weight Kurare Poval PVA-110 manufactured by Kuraray Co., Ltd. and 0.1% by weight Emarex 710 manufactured by Nippon Emulsion K.K. was prepared as the protective layer coating liquid 1. In addition, the coating liquid was coated such that the solid component amount of the protective layer formed became 1.0 g/m$^2$.

(Protective Layer Coating Liquid 2: The Protective Layer Coating Liquid PC-5 Described in the Example of Japanese Patent Application No. 2000-65238 as Described Above.)

After dissolving the materials shown below in a mixed solvent of isopropanol/methyl ethyl ketone (70/30 Vol. %), a matting agent and a lubricant were added and dispersed by a high-speed homogenizer to obtain the protective layer coating liquid 2. As the matting agent, Saisilia 431 (synthetic silica: mean particle size 2.5 μm) manufactured by Fuji Silisia Kagaku K.K.) was used, as the lubricant, Celozole 524 (main component: carnauba wax) manufactured by Chukyo Yushi K.K. was used, as a coating aid, Megafac F176P (fluorine-base polymer) manufactured by Dainippon Ink & Chemicals, Inc. was used, and as a plasticizer, CS-12 manufactured by CHISSO CORPORATION was used.

| | |
|---|---|
| Binder (ethyl methacrylate/2-hydroxyethyl methacrylate (6/4 weight ratio) copolymer) | 1.5 g/m$^2$ |
| Matting agent | 60 mg/m$^2$ |
| Lubricant | 0.2 g/m$^2$ |
| Coating aid | 6.9 mg/m$^2$ |
| Plasticizer | 0.3 g/m$^2$ |

(Protective Layer Coating Liquid 3: The Protective Layer Coating Liquid PC-6 Described in the Example of Japanese Patent Application No. 2000-65238 as Described Above.)

After preparing an aqueous dispersion of the materials shown below, the dispersion was stirred for 30 minutes to obtained the protective layer coating liquid 3. As the latex, AS-563A manufactured by Daicel Chemical Industries, Ltd., was used, as the fluorine-containing surface active agent, Megafac F120 manufactured by Dainippon Ink & Chemicals, Inc., was used, as the lubricant, Celozole 524 (main component: carnauba wax) manufactured by Chukyo Yushi K.K. was used, as polyvinyl alcohol, Kurare Poval PVA-235 manufactured by Kuraray Co., Ltd., was used, and the matting agent, SX-713 manufactured by Soken Kafaku K.K. was used.

| | |
|---|---|
| Latex | 2.5 g/m$^2$ |
| Matting agent | 60 mg/m$^2$ |
| Lubricant | 0.2 g/m$^2$ |
| Fluorine-containing surfactant | 6.9 mg/m$^2$ |
| Polyvinyl alcohol | 0.3 g/m$^2$ |

<Processing Condition of Image Formation>

About each of the image-forming materials 1 to 6 thus obtained, the image-forming characteristics of the heat or light inductive property (heat mode light) were determined by a laser-irradiation test. For the laser exposure, two Specra Diode Labs No. SDL-2430 laser oscillators (wavelength region: 800 to 830 nm) were combined to give the output of 140 mW and were used as an imaging laser light. By using the laser light, the beam diameter was established to 20 μm and the irradiation energy density of the laser light on the sample was established to 4.5 mJ/mm$^2$. After performing the scanning exposure from the protective layer side of the image-forming material under the laser exposure conditions, the color density at 410 nm at the image-forming material sample was measured. The measurement results are shown in Table 3.

Also, after allowing to stand for 7 days each image-forming material sample under a non-humidity condition (expressed as dry) at 45° C. or under the humidity condition of a humidity of 70% at 45° C., the color density by fog at 410 nm of the image-forming material sample was measured, and the increased value of the fog density from that immediately after the preparation of the each sample was obtained. The results are shown in Table 4.

From the test results of the image-forming faculty in Table 3 and the test results of the storage stability in Table 4, the image-forming material of the invention have both the good image-recording property and the good storage stability such that the increase of the fog density during test with the passage of time is remarkably less and by the laser light irradiation, a sufficient color density is obtained. Furthermore, by the visual inspection of the image-forming materials after the laser light irradiation, the samples 1 to 4 of the invention show almost no haze and have a large durability to thermal breakdown, on the other hand, in the samples 4 and 5 of the comparative examples, the haze is high and even in the point, the usefulness of the image-forming materials of the invention is shown.

TABLE 2

| Sample | Acid-generating Agent 3 mmol/m$^2$ | Coloring agent 1 mmol/m$^2$ | IR dye 0.12 mmol/m$^2$ | Binder 1 g/m$^2$ |
|---|---|---|---|---|
| 1 | (1) | LD-1 | IR-1 | Polystyrene |
| 2 | (2) | LD-1 | IR-1 | Polystyrene |
| 3 | P-1 | LD-1 | IR-1 | none |
| 4 | P-2 | LD-1 | IR-1 | none |
| 5 | R-1 | LD-1 | IR-1 | Polystyrene |
| 6 | R-2 | LD-1 | IR-1 | none |

In Table 2, Sample Nos. 1 to 4 are the samples of the invention and Sample Nos. 5 and 6 are the sample of the comparative examples.

TABLE 3

| Sample | Color Density | Note |
|---|---|---|
| 1 | 1.36 | Invention |
| 2 | 1.29 | Invention |
| 3 | 2.16 | Invention |
| 4 | 2.08 | Invention |
| 5 | 1.31 | Comparative Example |
| 6 | 2.12 | Comparative Example |

TABLE 4

| Sample | 45° C.-Dry | 45° C.-Humidity 70% RH | Note |
|---|---|---|---|
| 1 | 0.01 | 0.02 | Invention |
| 2 | 0.00 | 0.01 | Invention |
| 3 | 0.01 | 0.03 | Invention |
| 4 | 0.01 | 0.01 | Invention |
| 5 | 0.32 | 0.56 | Comparative Example |
| 6 | 0.68 | 0.97 | Comparative Example |

The numerals each shows the increase of the color density at 410 nm from coating after the time passage test (7 days).

The compounds shown in Table 2 are as follows. Comparative compounds:

(R-1)

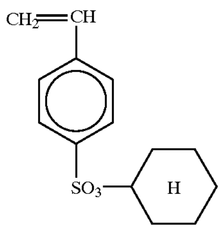

(R-2)

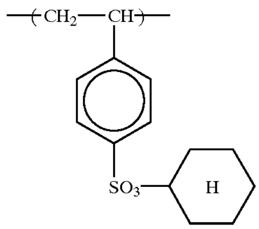

Weight average molecular weight 57,000

IR-4

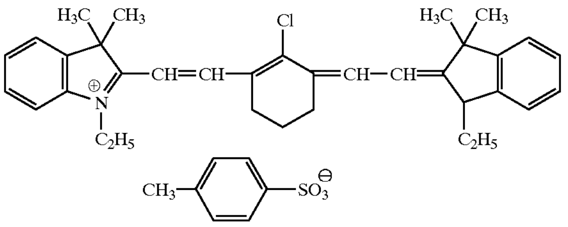

Example 2

It is shown below that when the acid-generating agent of the invention is copolymerized with a leuco dye, an excellent performance can be obtained.

Each of the compounds shown in Table 5 (the coating amount is described in Table 5 and the structures of the comparative compounds are described in Table 6) was dissolved in chloroform and the solution was coated on a polyethylene terephthalate having a thickness of 175 μm. On each of the films was coated the protective layer coating liquid described in Example 1 such that the solid component amount of the protective layer formed became 1.0 g/$m^2$ to prepare image-forming materials 7 to 10.

Each of the image-forming materials 7 to 10 thus prepared was subjected to the laser exposure under the same conditions as in Example 1 and the color density at 410 nm was measured (Table 7). Furthermore, each of the coated samples of the image-forming materials 7 to 10 prepared was allowed to stand for 7 days under the conditions of 45° C., dry (means no humidity as described above) or under the conditions of 45° C. and a humidity of 70% RH, and the fog density at 410 nm of each sample was determined (Table 8). From Table 7 and Table 8, in the samples 7 and 8 each using the compound of the invention, the fog density is low and each sample is excellent in the shelf life, as well as the color density is sufficiently high, whereby the usefulness of the compounds of the invention is clear.

On the other hand, in the samples 9 and 10 of the comparative examples, the color density is almost same as that of the samples of the invention, but the formation of fog with the passage of time is greatly increased, which results in giving an insufficient discriminating faculty.

TABLE 5

| Sample | Copolymer coloring agent Leuco dye portion 2 mmol/$m^2$ | IR Dye 0.12 mmol/$m^2$ |
|---|---|---|
| 7 | CP-4 | IR-1 |
| 8 | CP-9 | IR-1 |
| 9 | P-3 | IR-1 |
| 10 | P-4 | IR-1 |

Samples 7 and 9: Samples of the invention
Samples 9 and 10: Samples of the comparative examples

TABLE 6

| Sample | A | B | C | x | y | z |
|---|---|---|---|---|---|---|
| R-(3) | R-1 | R-(3) | — | 75 | 25 | |
| R-(4) | R-1 | R-(19) | — | 20 | 80 | |

R-3 Weight average molecular weight 38,000
R-4 Weight average molecular weight 42,000

TABLE 7

| Sample | Coloring Density | Note |
|---|---|---|
| 7 | 3.82 | Invention |
| 8 | 2.54 | Invention |
| 9 | 3.79 | Comparative Example |
| 10 | 2.51 | Comparative Example |

TABLE 8

| Sample | 45° C.-Dry | 45° C.-Humidity 70% RH | Note |
|---|---|---|---|
| 7 | 0.01 | 0.02 | Invention |
| 8 | 0.02 | 0.03 | Invention |
| 9 | 0.58 | 0.98 | Comparative Example |
| 10 | 0.63 | 1.42 | Comparative Example |

The numerals show the increased values of the fog density at 410 nm for 7 days directly after the preparation of the each sample.

Example 3

In Example 3, the comparison of the thermal decomposition temperature between the compound of the invention and a comparative compound having a structure similar to the structure of the compound was carried out. As the compounds of the invention, the thermal decomposition temperatures of the compounds (1) to (8) shown in the above-described Synthesis examples are from 165 to 192° C. as shown in the synthesis examples. As the known comparative compounds, R-1 and R-2 shown in Example 1 were synthesized. In these compounds, a polymerizable group is bonded to the sulfonic acid site of sulfonic acid ester (the portion corresponding to $R^1$ represented in the formula (I)), and R-1 is a monomer and R-2 is a polymer obtained by polymerizing the monomer. The thermal decomposition temperatures of them were 133° C. and 112° C. respectively and the decomposition temperatures were low, and they were unstable. In spite of that the above-described compounds of the invention had the structures similar to those of the above-described comparative compounds, the thermal decomposition temperatures thereof were higher than those of the comparative compounds by at least 32° C. and at most 80° C. (the thermal decomposition temperatures are described in the synthesis examples) and they were stable. As described above, it has been found the very useful designs that in spite of having similar structures to those of the known compounds, in the compounds of the invention, the thermal decomposition temperatures can be increased in the invention.

Example 4

Each of the monomers of the invention and the monomer of the comparative example was polymerized to synthesize the polymers represented by the following formula (A), wherein A represents an acid-generating agent and the numerals of 70 and 30 each represents the mole ratio of each monomer. The synthesis of the polymer carried out by mixing the monomers constituting each polymer at the molar ratio of 70:30 in toluene and polymerizing them by a radical polymerization. The polymerization reaction was carried out by the same method as the synthesis example of the homopolymer (P-1) described above.

(A)

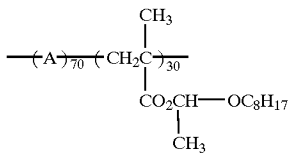

The synthesized polymers are shown in Table 9.

Each of the polymers and the IR dye shown in Example 1 were dissolved in chloroform and the solution was coated on a polyethylene phthalate film having a thickness of 175 μm such that the amount of the acid-generating agent becomes 5 $mmol/m^2$ and the amount of the IR dye becomes 0.15 $mmol/m^2$.

The image-recording characteristics of the heat or light inductive property (heat mode light) of the image-forming material thus obtained were determined by a laser light irradiation test. For the laser exposure, two Specta Diode Labs No. SDL-2430 laser oscillators (wavelength region: 800 to 830 nm) were combined to give the output of 140 mW and were used as an imaging laser light. By using the laser light, the beam diameter was established to 20 μm and the irradiation energy density of the laser light on the sample was established to 4.5 $mJ/mm^2$. After performing the scanning exposure from the protective layer side of the image-forming material under the laser exposure conditions, a heat development was carried out at 120° C. for 30 seconds, the infrared absorption change of the polymer ester was determined, and the reactivity was evaluated.

Also, after allowing to stand for 7 days each image-forming material sample under a non-humidity condition (expressed as dry) at 45° C. or under the humidity condition of a humidity of 70% at 45° C., the fading ratio of the polymer ester was measured and the shelf life of each sample was evaluated.

For the evaluations of the shelf life and the reactivity, the IR absorption of each film was measured, and the IR (1640 nm) absorption intensity of the image-forming material directly after the preparation thereof was defined as 100%, the evaluation was calculated by the fading ratio of the absorption (1640 nm) of the ester (Tables 10 and 11). The fading ratio of the IR absorption of the image-forming material directly preparation thereof by a laser light shows a higher activity as the value is smaller by the measure of the activity of the acid-generating reaction by the irradiation of a heat mode light, and the fading ratio of the IR absorption of the same with the passage of time shows more stability as the value of the measure of fading by decomposition with the passage of time, that is, the stability is larger.

As is clear from the results of Table 10 and Table 11, the image-forming materials using the monomers of the invention have excellent reactivity and excellent storage stability and the usefulness of the compounds of the invention for the image-forming materials using acid generation, as the trigger is clear.

TABLE 9

| | Acid-generating Agent | | | |
|---|---|---|---|---|
| Sample | Structure | Monomer component | IR Dye | Note |
| 1 | Formula (A) | (1) | IR-1 | Invention |
| 2 | Formula (A) | (2) | IR-1 | Invention |
| 3 | Formula (A) | R-1 | IR-1 | Comparison Example |

TABLE 10

| Sample | Fading Ratio of Ester (%) | Note |
|---|---|---|
| 1 | 100 | Invention |
| 2 | 100 | Invention |
| 3 | 100 | Comparison Example |

TABLE 11

| Sample | 45° C.-Dry | 45° C.-Humidity 70% | Note |
|---|---|---|---|
| 1 | 99 | 97 | Invention |
| 2 | 100 | 99 | Invention |
| 3 | 63 | 18 | Comparative Example |

(Note)
The numeral in the table shows the residual ratio (%) of the ester during storage with the passage of time.

As described above, the image-forming material comprising on a support the acid-generating agent of the invention shown by the formula (I) or the polymer obtained by polymerizing the acid-generating agent and a compound causing the light absorption change in the absorption region of from 360 to 700 nm by the action of an acid has a high sensitivity and an excellent storage stability, which result in increasing the discrimination faculty of the image portions and the non-image portions. In particular, the image-forming material is suitable for scanning-type image recording by the irradiation of a laser light.

Also, the sulfonic acid ester of the invention generating an acid by the action of light or heat and the polymerized product thereof are stable during storage as compared acid-generating agents of prior art, sensitively response to heat and heat mode light, and show a high discriminating property of the light-irradiated region and the light-non-irradiated region. Accordingly, the material can be widely used as the image-forming materials giving high image quality as well as an image-forming means together with a substance of causing the change of the properties, and particularly the change of color and the change of the hydrophilic property to hydrophobic property, by the acid.

While the invention has been described in detail and with reference to specific embodiments thereof, it will be apparent to one skilled in the art that various changes and modifications can be made therein without departing from the spirit and scope thereof.

What is claimed is:

1. An image-forming material comprising on a support an acid-generating agent represented by following formula (I) generating an acid by the action of heat or a polymer obtained by polymerizing the acid-generating agent and a compound causing a change in the absorption region of 360 to 700 nm by an intramolecular or intermolecular reaction by the action of an acid, (I)

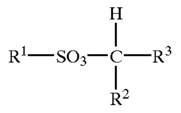

wherein $R^1$ represents an alkyl group, an aryl group, or a heterocyclic group, $R^2$ and $R^3$ each independently represents an alkyl group or an aryl group, excluding that $R^2$ and $R^3$ are simultaneously aryl groups, $R^2$ and $R^3$ may combine to form a ring, and at least one of $R^2$ and $R^3$ has a polymerizing unsaturated group.

2. The image-forming material according to claim 1, wherein the acid-generating agent represented by the formula (I) is represented by following formula (II):

(II)

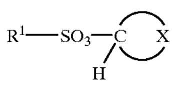

wherein $R^1$ has the same meaning as in the formula (I) and X represents an atomic group necessary for forming a ring together with C, and at least one of the atomic group constituting X has a polymerizing unsaturated group.

3. The image-forming material according to claim 1 or 2, wherein the image-forming material comprises a polymer having a partial structure made of the acid-generating agent represented by the formula (I) or (II) as a repeating unit.

4. The image-forming material according to claim 3, wherein the polymer is a polymer represented by following formula (III):

$$-(A)_x-(B)_y-(C)_z- \quad \text{(III)}$$

wherein A represents a repeating unit obtained by polymerizing the acid-generating agent represented by the formula (I) or (II), B represents a repeating unit obtained by polymerizing at least one kind of a vinyl monomer having a partial structure causing a change in the absorption region of from 360 to 700 by the action of an acid, C represents a repeating unit obtained by polymerizing at least one kind of a vinyl monomer copolymerizing with A and C, x, y and z represent mol %, each represents $1 \leqq x \leqq 100$, $0 \leqq y \leqq 99$, $0 \leqq z \leqq 99$, and $x+y+z=100$.

5. The image-forming material according to claim 1, 2, or 4, wherein the image-forming material comprises an infrared absorbing dye and forms images by the irradiation of an infrared laser light.

6. The image-forming material according to claim 3, wherein the image-forming material comprises an infrared absorbing dye and forms images by the irradiation of an infrared laser light.

7. The image-forming material according to claim 1, 2 or 4, wherein the image-forming layer does not comprise silver compound or a salt thereof.

8. The image-forming material according to claim 3 wherein the image-forming layer does not comprise silver compound or a salt thereof.

9. The image-forming material according to claim 5 wherein the image-forming layer does not comprise silver compound or a salt thereof.

10. The image-forming material according to claim 6 wherein the image-forming layer does not comprise silver compound or a salt thereof.

11. A sulfonic acid ester derivative represented by following formula (II):

(II)

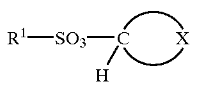

wherein $R^1$ represents an alkyl group, an aryl group, or a heterocyclic group, X represents an atomic group necessary for forming a ring together with C, and at least one of the atomic group constituting X has a polymerizing unsaturated group.

12. A sulfonic acid ester derivative according to claim 11, wherein the sulfonic acid ester derivative represented by formula (II) is represented by following formula (IV):

(IV)

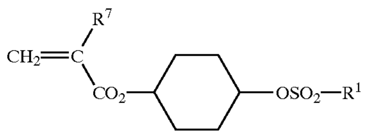

wherein $R^1$ represents an alkyl group, an aryl group, or a heterocyclic group, and $R^7$ represents a hydrogen atom or an alkyl group which can have a substituent.

13. A polymer obtained by polymerizing a sulfonic acid ester derivative represented by following formula (I) or (II):

(I)

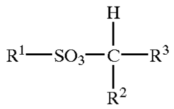

wherein $R^1$ represents an alkyl group, an aryl group, or a heterocyclic group, $R^2$ and $R^3$ each independently represents an alkyl group or an aryl group, excluding that $R^2$ and $R^3$ are simultaneously aryl groups, $R^2$ and $R^3$ may combine to form a ring, and at least one of $R^2$ and $R^3$ has a polymerizing unsaturated group, and (II)

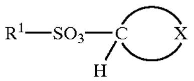

wherein $R^1$ has the same meaning as in the formula (I), X represents an atomic group necessary for forming a ring together with C, and at least one of the atomic group constituting X has a polymerizing unsaturated group.

* * * * *